United States Patent
Futatsugi

(10) Patent No.: US 10,188,653 B2
(45) Date of Patent: *Jan. 29, 2019

(54) DIACYLGLYCEROL ACYLTRANSFERASE 2 INHIBITORS

(71) Applicant: Pfizer Inc., New York, NY (US)

(72) Inventor: Kentaro Futatsugi, Quincy, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,785

(22) Filed: Sep. 1, 2017

(65) Prior Publication Data

US 2018/0042926 A1    Feb. 15, 2018

Related U.S. Application Data

(60) Continuation of application No. 15/193,440, filed on Jun. 27, 2016, now Pat. No. 9,789,110, which is a division of application No. 14/643,210, filed on Mar. 10, 2015, now Pat. No. 9,440,949.

(60) Provisional application No. 61/954,351, filed on Mar. 17, 2014.

(51) Int. Cl.

| | |
|---|---|
| *A61K 31/506* | (2006.01) |
| *A61K 31/5377* | (2006.01) |
| *A61K 31/606* | (2006.01) |
| *A61K 31/4545* | (2006.01) |
| *A61K 45/06* | (2006.01) |
| *C07D 491/08* | (2006.01) |
| *C07D 487/02* | (2006.01) |
| *C07D 413/14* | (2006.01) |
| *C07D 401/14* | (2006.01) |
| *C07D 487/04* | (2006.01) |
| *C07D 401/04* | (2006.01) |

(52) U.S. Cl.
CPC ........ *A61K 31/506* (2013.01); *A61K 31/4545* (2013.01); *A61K 31/5377* (2013.01); *A61K 31/606* (2013.01); *A61K 45/06* (2013.01); *C07D 401/04* (2013.01); *C07D 401/14* (2013.01); *C07D 413/14* (2013.01); *C07D 487/02* (2013.01); *C07D 487/04* (2013.01); *C07D 491/08* (2013.01)

(58) Field of Classification Search
CPC .. C07D 401/04; C07D 401/14; C07D 487/04; C07D 413/14; C07D 487/02; C07D 491/08; A61K 45/06; A61K 31/506; A61K 31/4545; A61K 31/5377; A61K 31/606

See application file for complete search history.

(56) References Cited

U.S. PATENT DOCUMENTS

| | | | |
|---|---|---|---|
| 9,296,745 B2 | 3/2016 | Ahn et al. | |
| 9,440,949 B2 | 9/2016 | Cabral et al. | |
| 9,789,110 B2 * | 10/2017 | Futatsugi | ............. C07D 401/04 |

FOREIGN PATENT DOCUMENTS

| | | |
|---|---|---|
| WO | 2010/056506 | 5/2010 |
| WO | 2012/024179 | 2/2012 |
| WO | 2012/164071 | 12/2012 |
| WO | 2013/068328 | 5/2013 |
| WO | 2013/150416 | 10/2013 |

OTHER PUBLICATIONS

Zhigang Wang et al., Involvement and Mechanism of DGAT2 upregulation in the Pathogenesis of Alcoholic Fatty Liver Disease, Journal of Lipid Research, vol. 51, 2010.*

* cited by examiner

*Primary Examiner* — Alexander R Pagano
*Assistant Examiner* — Ebenezer O Sackey
(74) *Attorney, Agent, or Firm* — A. Dean Olson

(57) ABSTRACT

Compounds of Formula I that inhibit the activity of the diacylglycerol acyltransferase 2 (DGAT2) and their uses in the treatment of diseases linked thereto in animals are described herein.

4 Claims, 3 Drawing Sheets

FIG.1 (REPLACEMENT SHEET)

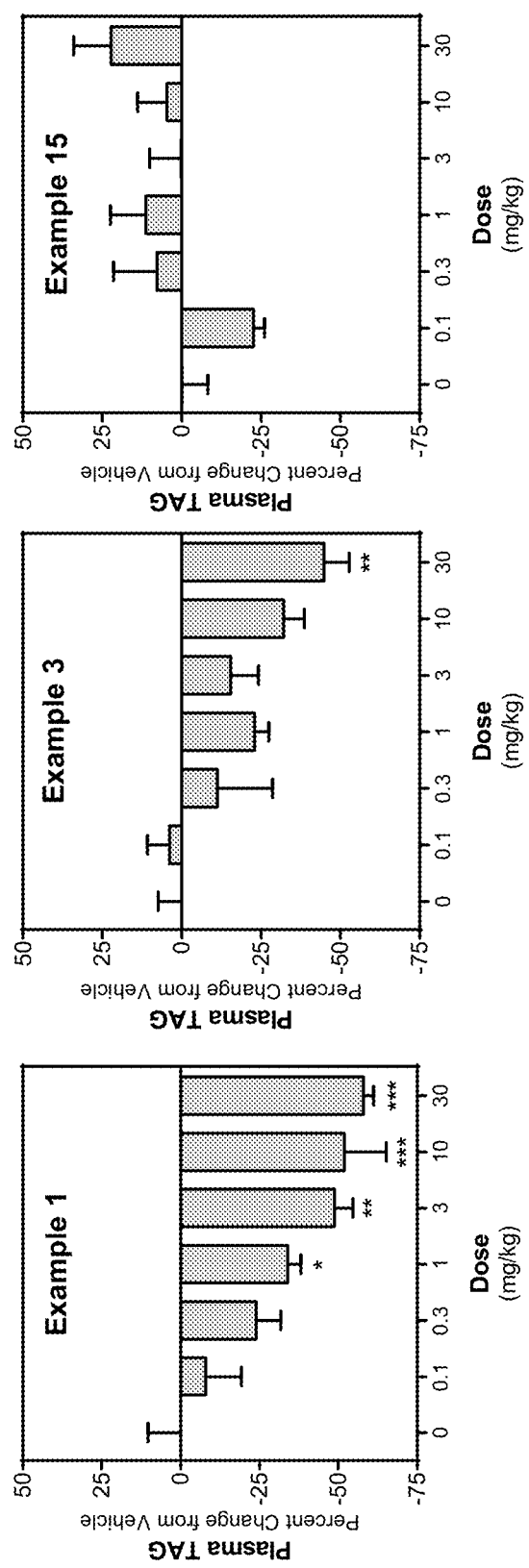
FIG. 3 (REPLACEMENT SHEET)

DIACYLGLYCEROL ACYLTRANSFERASE 2 INHIBITORS

FIELD OF THE INVENTION

The present invention relates to new pharmaceutical compounds, pharmaceutical compositions containing these compounds, and their use to inhibit the activity of the diacylglycerol acyltransferase 2 (DGAT2).

BACKGROUND OF THE INVENTION

Triglycerides or triacylglycerols (TAG) represent a major form of energy storage in mammals. TAG's are formed by the sequential esterification of glycerol with three fatty acids of varying chain lengths and degrees of saturation (1). TAG synthesized in the intestine or liver are packaged into chylomicrons or very low-density lipoprotein (VLDL), respectively, and exported to peripheral tissues where they are hydrolysed to their constituent fatty acids and glycerol by lipoprotein lipase (LPL). The resultant non-esterified fatty acids (NEFA) can either be metabolised further to produce energy or reesterified and stored.

Under normal physiological conditions, the energy-dense TAG remains sequestered in various adipose depots until there is a demand for its release, whereupon, it is hydrolyzed to glycerol and free fatty acids which are then released into the blood stream. This process is tightly regulated by the opposing actions of insulin and hormones such as catecholamines which promote the deposition and mobilization of TAG stores under various physiological conditions. In the post-prandial setting, insulin acts to inhibit lipolysis, thereby, restraining the release of energy in the form of NEFA and ensuring the appropriate storage of dietary lipids in adipose depots. However, in patients with type 2 diabetes, the ability of insulin to suppress lipolysis is ameliorated and NEFA flux from adipocytes is inappropriately elevated. This, in turn, results in increased delivery of lipid to tissues such as muscle and liver. In the absence of energetic demand the TAG and other lipid metabolites, such as diacylglycerol (DAG) can accumulate and cause a loss of insulin sensitivity (2). Insulin resistance in muscle is characterized by reduced glucose uptake and glycogen storage, whilst in the liver, loss of insulin signaling gives rise to dysregulated glucose output and over-production of TAG-rich VLDL, a hallmark of type 2 diabetes (3). Elevated secretion of TAG-enriched VLDL, so called VLDL1 particles, is thought to stimulate the production of small, dense low-density lipoprotein (sdLDL), a proatherogenic subfraction of LDL that is associated with elevated risk of coronary heart disease (4).

Diacylglycerol acyltransferases (DGAT) catalyze the terminal step in TAG synthesis, specifically, the esterification of a fatty acid with diacylglycerol resulting in the formation of TAG. In mammals, two DGAT enzymes (DGAT1 and DGAT2) have been characterized. Although these enzymes catalyze the same enzymatic reaction their respective amino acid sequences are unrelated and they occupy distinct gene families. Mice harboring a disruption in the gene encoding DGAT1 are resistant to diet-induced obesity and have elevated energy expenditure and activity (5). Dgat1−/− mice exhibit dysregulated postaborpative release of chylomicrons and accumulate lipid in the enterocytes (6). The metabolically favorable phenotype observed in these mice is suggested to be driven by loss of DGAT1 expression in the intestine (7). Importantly, despite a defect in lactation in female Dgat1−/− mice, these animals retain the capacity to synthesize TAG suggesting the existence of additional DGAT enzymes. This observation and the isolation of a second DGAT from the fungus *Mortierella rammaniana* led to the identification and characterization of DGAT2 (8).

DGAT2 is highly expressed in liver and adipose, and unlike DGAT1, exhibits exquisite substrate specificity for DAG (8). Deletion of the DGAT2 gene in rodents results in defective intrauterine growth, severe lipemia, impaired skin barrier function, and early post-natal death (9). Due to the lethality caused by loss of DGAT2, much of our understanding of the physiological role of DGAT2 derives from studies performed with antisense oligonucleotides (ASO) in rodent models of metabolic disease. In this setting, inhibition of hepatic DGAT2 resulted in improvements in plasma lipoprotein profile (decrease in total cholesterol and TAG) and a reduction of hepatic lipid burden which was accompanied by improved insulin sensitivity and whole-body glucose control (10-12). Although the molecular mechanisms underlying these observations are not fully elucidated, it is clear that suppression of DGAT2 results in a down-regulation of the expression of multiple genes encoding proteins involved in lipogensis, including sterol regulatory element-binding proteins 1c (SREBP1c) and stearoyl CoA-desaturase 1 (SCD1) (11, 12). In parallel, oxidative pathways are induced as evidenced by increased expression of genes such as carnitine palmitoyl transfersase 1 (CPT1) (11). The net result of these changes is to decrease the levels of hepatic DAG and TAG lipid which, in turn, leads to improved insulin responsiveness in the liver. Furthermore, DGAT2 inhibition suppresses hepatic VLDL TAG secretion and reduction in circulating cholesterol levels. Finally, plasma apolipoprotein B (APOB) levels were suppressed, possibly due to decreased supply of TAG for lipidation of the newly synthesized APOB protein (10, 12). The beneficial effects of DGAT2 inhibition on both glycemic control and plasma cholesterol profile suggest that this target might be valuable in the treatment of metabolic disease (11). In addition, the observation that suppression of DGAT2 activity results in reduced hepatic lipid accumulation suggests that inhibitors of this enzyme might have utility in the treatment of non-alcoholic steatohepatitis (NASH), a highly prevalent liver disease characterized by the deposition of excess fat in the liver.

1. Coleman, R. A., and D. G. Mashek. 2011. Mammalian triacylglycerol metabolism: synthesis, lipolysis, and signaling. *Chem Rev* 111: 6359-6386.
2. Erion, D. M., and G. I. Shulman. 2010. Diacylglycerol-mediated insulin resistance. *Nat Med* 16: 400-402.
3. Choi, S. H., and H. N. Ginsberg. 2011. Increased very low density lipoprotein (VLDL) secretion, hepatic steatosis, and insulin resistance. *Trends Endocrinol Metab* 22: 353-363.
4. St-Pierre, A. C., B. Cantin, G. R. Dagenais, P. Mauriege, P. M. Bernard, J. P. Despres, and B. Lamarche. 2005. Low-density lipoprotein subfractions and the long-term risk of ischemic heart disease in men: 13-year follow-up data from the Quebec Cardiovascular Study. *Arterioscler Thromb Vasc Biol* 25: 553-559.
5. Smith, S. J., S. Cases, D. R. Jensen, H. C. Chen, E. Sande, B. Tow, D. A. Sanan, J. Raber, R. H. Eckel, and R. V. Farese, Jr. 2000. Obesity resistance and multiple mechanisms of triglyceride synthesis in mice lacking Dgat. *Nat Genet* 25: 87-90.
6. Buhman, K. K., S. J. Smith, S. J. Stone, J. J. Repa, J. S. Wong, F. F. Knapp, Jr., B. J. Burri, R. L. Hamilton, N. A. Abumrad, and R. V. Farese, Jr. 2002. DGAT1 is not essential for intestinal triacylglycerol absorption or chylomicron synthesis. *J Biol Chem* 277: 25474-25479.

7. Lee, B., A. M. Fast, J. Zhu, J. X. Cheng, and K. K. Buhman. 2010. Intestine-specific expression of acyl CoA:diacylglycerol acyltransferase 1 reverses resistance to diet-induced hepatic steatosis and obesity in Dgat1−/− mice. *J Lipid Res* 51: 1770-1780.

8. Yen, C. L., S. J. Stone, S. Koliwad, C. Harris, and R. V. Farese, Jr. 2008. Thematic review series: glycerolipids. DGAT enzymes and triacylglycerol biosynthesis. *J Lipid Res* 49: 2283-2301.

9. Stone, S. J., H. M. Myers, S. M. Watkins, B. E. Brown, K. R. Feingold, P. M. Elias, and R. V. Farese, Jr. 2004. Lipopenia and skin barrier abnormalities in DGAT2-deficient mice. *J Biol Chem* 279: 11767-11776.

10. Liu, Y., J. S. Millar, D. A. Cromley, M. Graham, R. Crooke, J. T. Billheimer, and D. J. Rader. 2008. Knockdown of acyl-CoA:diacylglycerol acyltransferase 2 with antisense oligonucleotide reduces VLDL TG and ApoB secretion in mice. *Biochim Biophys Acta* 1781: 97-104.

11. Choi, C. S., D. B. Savage, A. Kulkarni, X. X. Yu, Z. X. Liu, K. Morino, S. Kim, A. Distefano, V. T. Samuel, S. Neschen, D. Zhang, A. Wang, X. M. Zhang, M. Kahn, G. W. Cline, S. K. Pandey, J. G. Geisler, S. Bhanot, B. P. Monia, and G. I. Shulman. 2007. Suppression of diacylglycerol acyltransferase-2 (DGAT2), but not DGAT1, with antisense oligonucleotides reverses diet-induced hepatic steatosis and insulin resistance. *J Biol Chem* 282: 22678-22688.

12. Yu, X. X., S. F. Murray, S. K. Pandey, S. L. Booten, D. Bao, X. Z. Song, S. Kelly, S. Chen, R. McKay, B. P. Monia, and S. Bhanot. 2005. Antisense oligonucleotide reduction of DGAT2 expression improves hepatic steatosis and hyperlipidemia in obese mice. *Hepatology* 42: 362-371.

SUMMARY OF THE INVENTION

The present application is directed at compounds of Formula (I) and (Ia)

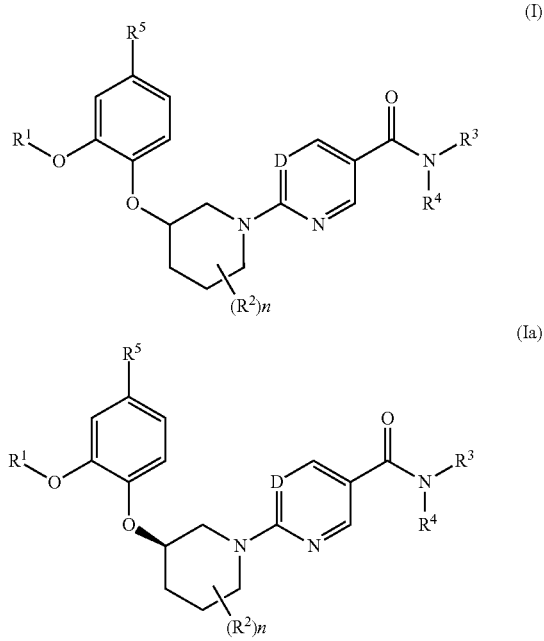

wherein:

D is N, CH, or CF;

$R^1$ is $(C_1-C_4)$alkyl optionally substituted with one, two or three substituents each independently selected from fluoro and $(C_3-C_6)$cycloalkyl;

$R^2$ is fluoro or $(C_1-C_4)$alkyl;

$R^3$ is H, $(C_1-C_4)$alkyl, or $(C_3-C_6)$cycloalkyl;

$R^4$ is H, $-((C_1-C_4)$alkyl$)_p$-$(C_3-C_6)$cycloalkyl, $-((C_1-C_4)$alkyl$)_p$-$(C_3-C_6)$heterocyclyl, $-((C_1-C_4)$alkyl$)_p$-aryl, or $-((C_1-C_4)$alkyl$)_p$-heteroaryl wherein $R^4$ is optionally substituted with one, two, three, or four substituents selected from halo, cyano, oxo, aminyl, iminyl, $-OH$, $-(C_1-C_4)$fluoroalkyl, $-(C_1-C_4)$alkoxy, $-(C_3-C_6)$cycloalkoxy, $-(C_1-C_4)$fluoroalkoxy, $-((C_1-C_4)$alkyl$)_q$-COOH, $-((C_1-C_4)$alkyl$)_q$-$(C_3-C_6)$cycloalkyl-COOH, $-((C_1-C_4)$alkyl$)_q$-$(C_3-C_6)$heterocyclyl-COOH, $-((C_1-C_4)$alkyl$)_q$-aryl-COOH, $-((C_1-C_4)$alkyl$)_q$-heteroaryl-COOH, $-O((C_1-C_4)$alkyl$)_q$-COOH, $-O((C_1-C_4)$alkyl$)_q$-aryl-COOH, $-O((C_1-C_4)$alkyl$)_q$-heteroaryl-COOH, $-((C_1-C_4)$alkyl$)_q$-$(C_3-C_6)$cycloalkyl, $-((C_1-C_4)$alkyl$)_q$-$(C_3-C_6)$heterocyclyl, $-((C_1-C_4)$alkyl$)_q$-aryl, $-((C_1-C_4)$alkyl$)_q$-heteroaryl, $-C(O)-(C_1-C_4)$alkyl, $-C(O)-(C_1-C_4)$alkoxy, $-C(O)-(C_3-C_6)$cycloalkyl, $-C(O)-(C_3-C_6)$heterocyclyl, $-C(O)-NR^6R^7$, $-C(O)-((C_1-C_4)$alkyl$)_q$-aryl, $-C(O)-((C_1-C_4)$alkyl$)_q$-heteroaryl, $-NR^6R^7$, $-NR^6-C(O)-R^7$, $-((C_1-C_4)$alkyl$)_q$-O-aryl, $-((C_1-C_4)$alkyl$)_q$-O-heteroaryl, $-S(O)_2-R^7$, and $-S(O)_2-NR^6R^7$;

or $R^3$ and $R^4$ may be joined together to form a 4- to 10-member fully saturated, or partially saturated ring system optionally substituted with one, two, three, or four substituents selected from halo, cyano, $-OH$, $-(C_1-C_4)$fluoroalkyl, $-(C_1-C_4)$alkoxy, $-(C_3-C_6)$cycloalkoxy, $-(C_1-C_4)$fluoroalkoxy, $-((C_1-C_4)$alkyl$)_q$-COOH, $-((C_1-C_4)$alkyl$)_q$-$(C_3-C_6)$cycloalkyl-COOH, $-((C_1-C_4)$alkyl$)_q$-$(C_3-C_6)$heterocyclyl-COOH, $C_4)$alkyl$)_q$-aryl-COOH, $-((C_1-C_4)$alkyl$)_q$-heteroaryl-COOH, $-O-((C_1-C_4)$alkyl$)_q$-COOH, $-O-((C_1-C_4)$alkyl$)_q$-aryl-COOH, $-O-((C_1-C_4)$alkyl$)_q$-heteroaryl-COOH, $-((C_1-C_4)$alkyl$)_q$-$(C_3-C_6)$cycloalkyl, $-((C_1-C_4)$alkyl$)_q$-$(C_3-C_6)$heterocyclyl, $-((C_1-C_4)$alkyl$)_q$-aryl, $-((C_1-C_4)$alkyl$)_q$-heteroaryl, $-C(O)-(C_1-C_4)$alkyl, $-C(O)-(C_3-C_6)$cycloalkyl, $-C(O)-(C_3-C_6)$heterocyclyl, $-C(O)$-aryl, $-C(O)-$heteroaryl, $-C(O)-NR^6R^7$, $-C(O)-(C_1-C_4)$alkyl-aryl, $-C(O)-(C_1-C_4)$alkyl-heteroaryl, $-NR^6R^7$, $-NR^6-C(O)-R^7$, $-O$-aryl, $-O$-heteroaryl, $-(C_1-C_4)$alkyl-O-aryl, $-(C_1-C_4)$alkyl-O-heteroaryl, $-O-(C_1-C_4)$alkyl-aryl, and $-O-(C_1-C_4)$alkyl-heteroaryl;

$R^5$ is H, F, or cyano;

$R^6$ is H, $(C_1-C_4)$alkyl, or $-S(O)_2-R^7$;

$R^7$ is H, $(C_1-C_4)$alkyl, $-(C_3-C_6)$cycloalkyl, $-(C_3-C_6)$heterocyclyl, aryl, or heteroaryl;

n is 0, 1, 2 or 3;

p is 0 or 1; and q is 0 or 1;

or a pharmaceutically acceptable salt thereof.

The present invention is also directed at pharmaceutical compositions that include a compound of Formula (I) or (Ia) or a pharmaceutically acceptable salt of said compound, present in a therapeutically effective amount, in admixture with at least one pharmaceutically acceptable excipient.

Furthermore, the present invention is directed at pharmaceutical compositions that include a compound of Formula (I) or (Ia) or a pharmaceutically acceptable salt of said compound, present in a therapeutically effective amount, in admixture with at least one pharmaceutically acceptable excipient and further including at least one additional pharmaceutical agent selected from the group consisting of an anti-obesity agent, an anti-diabetic agent, and a cholesterol/lipid modulating agent.

The present invention is also directed at a method for the treatment of diabetes comprising the administration of an effective amount of compound of Formula (I) or (Ia) or a pharmaceutically acceptable salt of said compound to a patient in need thereof.

The present invention is also directed at a method for treating a metabolic or metabolic-related disease, condition or disorder comprising the step of administering to a patient a therapeutically effective amount of a compound of Formula (I) or (Ia) or a pharmaceutically acceptable salt of said compound.

The present invention is also directed at a method for treating a metabolic or metabolic-related disease, condition or disorder comprising the step of administering to a patient in need of such treatment two separate pharmaceutical compositions comprising (i) a first pharmaceutical composition that includes a compound of Formula (I) or (Ia) or a pharmaceutically acceptable salt of said compound, present in a therapeutically effective amount, in admixture with at least one pharmaceutically acceptable excipient; and (ii) a second composition comprising at least one additional pharmaceutical agent selected from the group consisting of an anti-obesity agent and an anti-diabetic agent, and at least one pharmaceutically acceptable excipient.

It is to be understood that both the foregoing general description and the following detailed description are exemplary and explanatory only and are not restrictive of the invention, as claimed.

BRIEF DESCRIPTION OF THE DRAWINGS

FIG. 3 is acute effects of DGAT2 inhibitors on plasma TAG levels in Sprague Dawley rats for the Examples 1, 3 and 15.

DETAILED DESCRIPTION OF THE INVENTION

Figure 1:
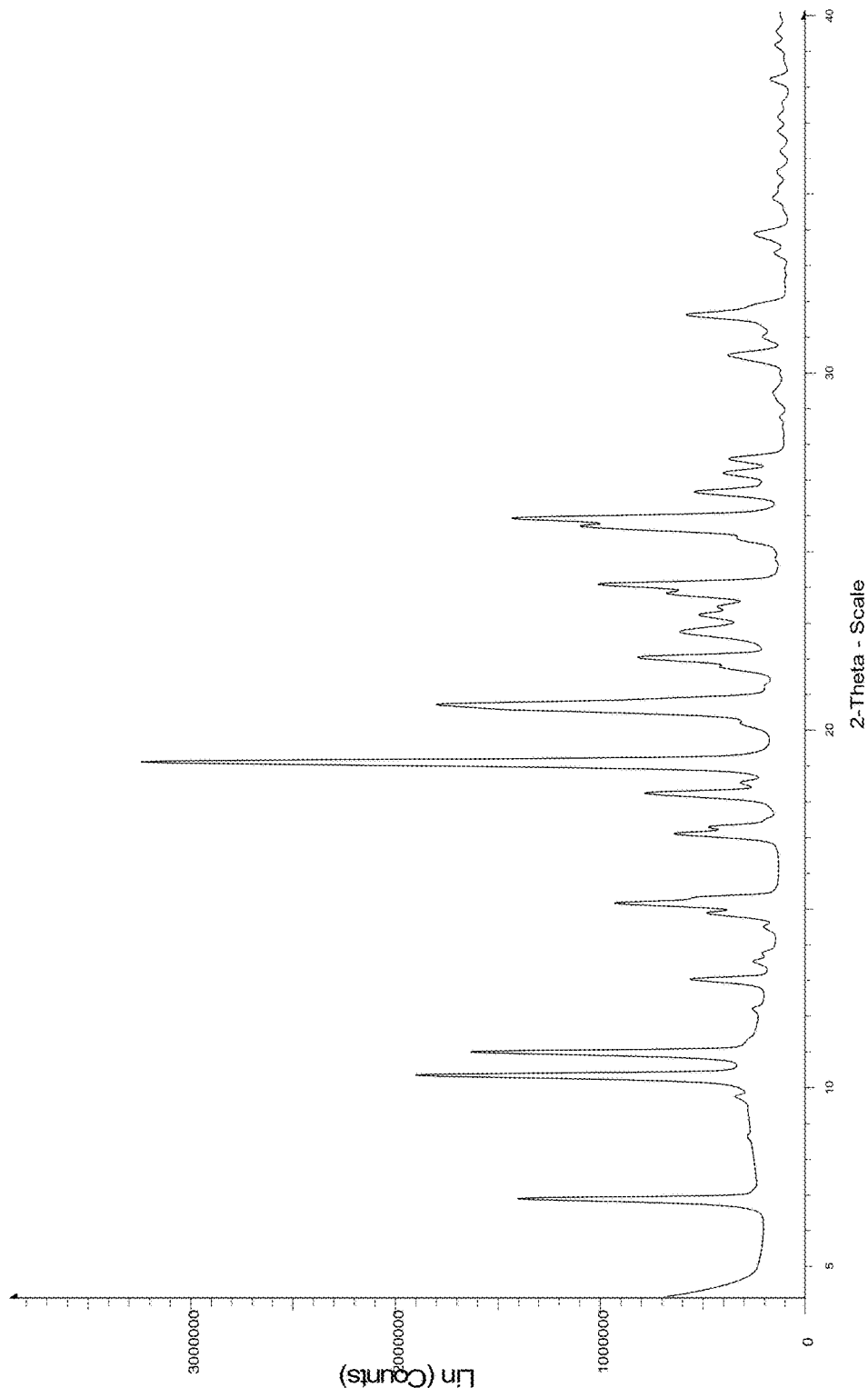
FIG. 1 is a characteristic x-ray powder diffraction pattern showing a crystalline form of Example 1 (Vertical Axis: Intensity (CPS); Horizontal Axis: Two theta (degrees)).

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, an arrowhead, "/" or wavy line, "⤳" denotes a point of attachment of a substituent to another group.

By "halo" or "halogen" is meant chloro, bromo, iodo, or fluoro.

"Fluroalkyl" or "fluoroalkoxy" refers to an alkyl or alkoxy group substituted with one or more fluoride atoms (e.g., fluoromethyl, difluoromethyl, trifluoromethyl, perfluoroethyl, 1,1-difluoroethyl and the like).

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, isobutyl, pentyl, isopentyl, neopentyl, tertiary pentyl, 1-methylbutyl, 2-methylbutyl, 3-methylbutyl, hexyl, isohexyl, heptyl and octyl.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl, and 1,2,3,4-tetrahydronaphthalenyl.

"Cycloalkyl" refers to a nonaromatic ring that is fully hydrogenated having one, two or three rings wherein such rings may be fused, wherein fused is defined above. Cycloalkyl also includes bicyclic structures that may be bridged or spirocyclic in nature with each individual ring within the bicycle varying from 3-8 atoms. Examples of such carbocyclic rings include cyclopropyl, cyclobutyl, cyclopentyl, and cyclohexyl.

By "cycloalkoxy" is meant cycloalkyl bonded through an oxy. Exemplary of such cycloalkoxy groups are cyclopropoxy, cyclobutoxy, cyclopentoxy and cyclohexoxy.

The term "heteroaryl" means an aromatic carbocyclic system containing one, two, three or four heteroatoms selected independently from oxygen, nitrogen and sulfur and having one, two or three rings wherein such rings may be fused, wherein fused is defined above. The term "heteroaryl" includes but is not limited to furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

The term "heterocyclyl" means a nonaromatic carbocyclic system containing one, two, three or four heteroatoms selected independently from oxygen, nitrogen and sulfur and having one, two or three rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O or S atoms. The term "heterocyclyl" includes but is not limited to lactones, lactams, cyclic ethers and cyclic amines, including the following exemplary ring systems: pyrrolidinonyl, 2,5-dihydro-1H-pyrrolyl, piperidinonyl, morpholinonyl, piperazinonyl, oxazolidinonyl, imidazolidinonyl, 1,3-oxazinan-2-onyl, tetrahydropyrimidin-2(1H)-onyl, epoxidyl, tetrahydrofuranyl, tetrahydropyranyl, dioxanyl, aziridinyl, azetidinyl, oxetanyl, pyrrolidinyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl and 2-oxa-6-azaspiro[3.3]heptanyl.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

"Patient" refers to warm blooded animals such as, for example, guinea pigs, mice, rats, gerbils, cats, rabbits, dogs, cattle, goats, sheep, horses, monkeys, chimpanzees, and humans.

By "pharmaceutically acceptable" is meant that the substance or composition must be compatible chemically and/or toxicologically, with the other ingredients comprising a formulation, and/or the mammal being treated therewith.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half life of the compound in the intestine and the second assay is for the half life of the compound in the liver.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the tetrazole moiety where the proton may migrate between the four ring nitrogen as follows.

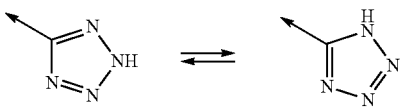

Valence tautomers include interconversions by reorganization of some of the bonding electrons.

Included within the scope of the claimed compounds present invention are all stereoisomers, geometric isomers and tautomeric forms of the compounds of Formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$, $^{124}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labelled compounds of Formula (I) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In one embodiment, D is N or C—F; and n is 0.

In another embodiment, $R^1$ is ethyl and $R^2$ is fluoro.

In a further embodiment, $R^5$ is H; $R^3$ is H; and $R^4$ is $(C_1-C_2)$alkyl-aryl, $(C_1-C_2)$alkyl-heteroaryl, or $(C_5-C_6)$cycloalkyl, wherein $R^4$ is optionally substituted with one, two, three, or four substituents selected from fluoro, chloro, cyano, —$((C_1-C_2)$alkyl$)_q$-COOH, —$(C_1-C_3)$alkyl, —$(C_3-C_6)$cycloalkyl, trifluoromethyl, difluoromethyl, —$(C_1-C_3)$alkoxy, -trifluoromethoxy, and difluoromethoxy.

In another embodiment, D is N or CH and $R^4$ is

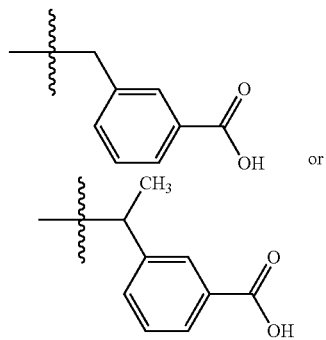

wherein $R^4$ is optionally substituted with one, two, or three substituents selected from fluoro, chloro, methyl, cyano, cyclopropyl, trifluoromethyl, difluoromethyl, methoxy, trifluoromethoxy, and difluoromethoxy.

One embodiment of the present invention is drawn to the compound:

2-(6-(3-(2-ethoxyphenoxy)piperidin-1-yl)-5-fluoronicotinamido)cyclopentane-1-carboxylic acid;
(1R,2S)-2-(6-((R)-3-(2-ethoxyphenoxy)piperidin-1-yl)-5-fluoronicotinamido)cyclopentane-1-carboxylic acid;
4-((2-(3-(2-ethoxyphenoxy)piperidin-1-yl)pyrimidine-5-carboxamido)methyl)-3-methylbenzoic acid;
(R)-4-((2-(3-(2-ethoxyphenoxy)piperidin-1-yl)pyrimidine-5-carboxamido)methyl)-3-methylbenzoic acid;
2-(2-(3-(2-ethoxyphenoxy)piperidin-1-yl)pyrimidine-5-carboxamido)cyclopentane-1-carboxylic acid; or
(1R,2S)-2-(2-((R)-3-(2-ethoxyphenoxy)piperidin-1-yl)pyrimidine-5-carboxamido)cyclopentane-1-carboxylic acid;
or a pharmaceutically acceptable salt thereof.

Another embodiment of the present invention is drawn to the compound:

3-((2-(3-(2-ethoxyphenoxy)piperidin-1-yl)pyrimidine-5-carboxamido)methyl)-4-methylbenzoic acid;
(R)-3-((2-(3-(2-ethoxyphenoxy)piperidin-1-yl)pyrimidine-5-carboxamido)methyl)-4-methylbenzoic acid;
3-((2-(3-(2-ethoxyphenoxy)piperidin-1-yl)pyrimidine-5-carboxamido)methyl)-5-methylbenzoic acid;
(R)-3-((2-(3-(2-ethoxyphenoxy)piperidin-1-yl)pyrimidine-5-carboxamido)methyl)-5-methylbenzoic acid;
3-((2-(3-(2-ethoxyphenoxy)piperidin-1-yl)pyrimidine-5-carboxamido)methyl)-2-methoxybenzoic acid;
(R)-3-((2-(3-(2-ethoxyphenoxy)piperidin-1-yl)pyrimidine-5-carboxamido)methyl)-2-methoxybenzoic acid;
3-(1-(2-(3-(2-ethoxyphenoxy)piperidin-1-yl)pyrimidine-5-carboxamido)ethyl)benzoic acid;
3-((R)-1-(2-((R)-3-(2-ethoxyphenoxy)piperidin-1-yl)pyrimidine-5-carboxamido)ethyl)benzoic acid;
3-((6-(3-(2-ethoxyphenoxy)piperidin-1-yl)nicotinamido)methyl)benzoic acid;
(R)-3-((6-(3-(2-ethoxyphenoxy)piperidin-1-yl)nicotinamido)methyl)benzoic acid;
3-((2-(3-(2-ethoxyphenoxy)piperidin-1-yl)pyrimidine-5-carboxamido)methyl)-4-methoxybenzoic acid;
(R)-3-((2-(3-(2-ethoxyphenoxy)piperidin-1-yl)pyrimidine-5-carboxamido)methyl)-4-methoxybenzoic acid;
3-((2-(3-(2-ethoxyphenoxy)piperidin-1-yl)pyrimidine-5-carboxamido)methyl)benzoic acid;
(R)-3-((2-(3-(2-ethoxyphenoxy)piperidin-1-yl)pyrimidine-5-carboxamido)methyl)benzoic acid;
3-((2-(3-(2-ethoxyphenoxy)piperidin-1-yl)pyrimidine-5-carboxamido)methyl)-4-fluorobenzoic acid;
(R)-3-((2-(3-(2-ethoxyphenoxy)piperidin-1-yl)pyrimidine-5-carboxamido)methyl)-4-fluorobenzoic acid;
3-((2-(3-(2-ethoxyphenoxy)piperidin-1-yl)pyrimidine-5-carboxamido)methyl)-5-methoxybenzoic acid; or
(R)-3-((2-(3-(2-ethoxyphenoxy)piperidin-1-yl)pyrimidine-5-carboxamido)methyl)-5-methoxybenzoic acid;
or a pharmaceutically acceptable salt thereof.

In a further embodiment, the compound of Formula (I) or (Ia) or a salt of the compound is present in a pharmaceutical composition in a therapeutically effective amount, in admixture with at least one pharmaceutically acceptable excipient.

In a further embodiment, the composition further includes at least one additional pharmaceutical agent selected from the group consisting of an anti-obesity agent, an anti-diabetic agent, and a cholesterol/lipid modulating agent.

In a further embodiment, the anti-obesity agent is selected from the group consisting of gut-selective MTP inhibitors (e.g., dirlotapide, mitratapide and implitapide, R56918, CCKa agonists, 5HT2c agonists, MCR4 agonist, lipase inhibitor, $PYY_{3-36}$, opioid antagonists, the combination of naltrexone with buprorion, oleoyl-estrone, obinepitide, pramlintide, tesofensine, leptin, liraglutide, bromocriptine, orlistat, exenatide, AOD-9604 phentermine and topiramate, and sibutramine.

In a further embodiment, the anti-diabetic agent is selected from the group consisting of an acetyl-CoA carboxylase-(ACC) inhibitor, a diacylglycerol O-acyltransferase 1 (DGAT-1) inhibitor, AZD7687, LCQ908, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist (a biguanide, a glucagon-like peptide 1 (GLP-1) modulator such as an agonist, liraglutide, albiglutide, exenatide, albiglutide, lixisenatide, dulaglutide, semaglutide, NN-9924, TTP-054, a protein tyrosine phosphatase-1B (PTP-1B) inhibitor, SIRT-1 activator, a dipeptidyl peptidease IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 (also termed GPBAR1) receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, and modulators of RXRalpha.

In a further embodiment, the cholesterol/lipid modulating agent is selected from the group consisting of HMG-CoA reductase inhibitors; squalene synthetase inhibitors; fibrates; bile acid sequestrants; ACAT inhibitors; MTP inhibitors; lipooxygenase inhibitors; choesterol absorption inhibitors; PCSK9 modulators and cholesteryl ester transfer protein inhibitors.

In an embodiment, the method for the treatment of diabetes includes the administration of an effective amount of compound of the present invention or a pharmaceutically acceptable salt of said compound to a patient in need thereof.

In another embodiment, the method for treating a metabolic or metabolic-related disease, condition or disorder includes the step of administering to a patient a therapeutically effective amount of a compound of the present invention or a pharmaceutically acceptable salt of said compound.

In another embodiment, the method for treating a condition selected from the group consisting of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD), includes the administration of an effective amount of a compound according to the present invention or a pharmaceutically acceptable salt of said compound.

In a further embodiment, the method for treating a metabolic or metabolic-related disease, condition or disorder includes the step of administering to a patient in need of such treatment two separate pharmaceutical compositions comprising (i) a first composition according to the present invention; and (ii) a second composition comprising at least one additional pharmaceutical agent selected from the group consisting of an anti-obesity agent and an anti-diabetic agent, and at least one pharmaceutically acceptable excipient.

In yet a further embodiment, the method of the present invention is performed when said first composition and said second composition are administered simultaneously.

In yet another embodiment, the method of the present invention is performed when first composition and said second composition are administered sequentially and in any order.

In one embodiment, when two compositions are administered, the first composition and the second composition are administered simultaneously. In another embodiment, the first composition and the second composition are administered sequentially and in any order.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)). Many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenyl-methylenoxycarbonyl (Fmoc) for amines and lower alkyl or benzyl esters for carboxylic acids) which are generally not chemically reactive under the reaction conditions described and can typically be removed without chemically altering other functionality in the Formula I and Ia compounds.

The Reaction Schemes described below are intended to provide a general description of the methodology employed in the preparation of the compounds of the present invention. Some of the compounds of the present invention contain a single chiral center with stereochemical designation (R). In the following Schemes, the general methods for the preparation of the compounds are shown either in racemic or enantioenriched form. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

In the Reaction Schemes that follow, the variables D, $R^1$, $R^2$, $R^3$, $R^4$, $R^5$ and n are as described in the summary except where otherwise noted.

Reaction Scheme I outlines the general procedures that can be used to provide compounds of the present invention having Formula (I). Those skilled in the art will recognize that Reaction Scheme I depicts the synthesis of racemic compounds, and that these routes may be adapted to the synthesis of either enantiomer of compounds of Formula (I).

Reaction Scheme I

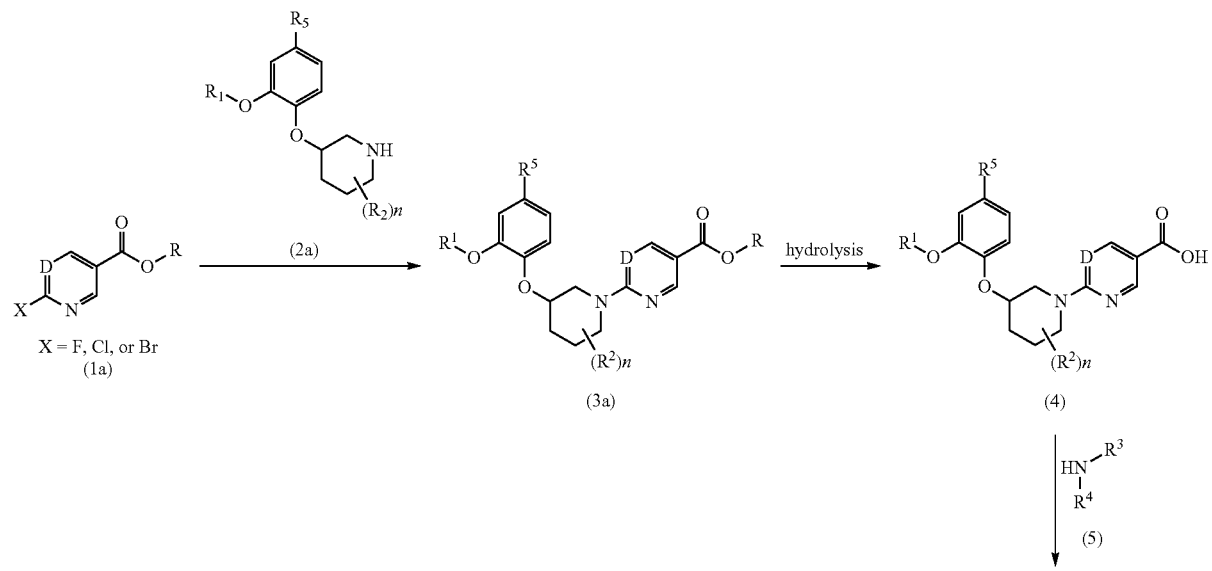

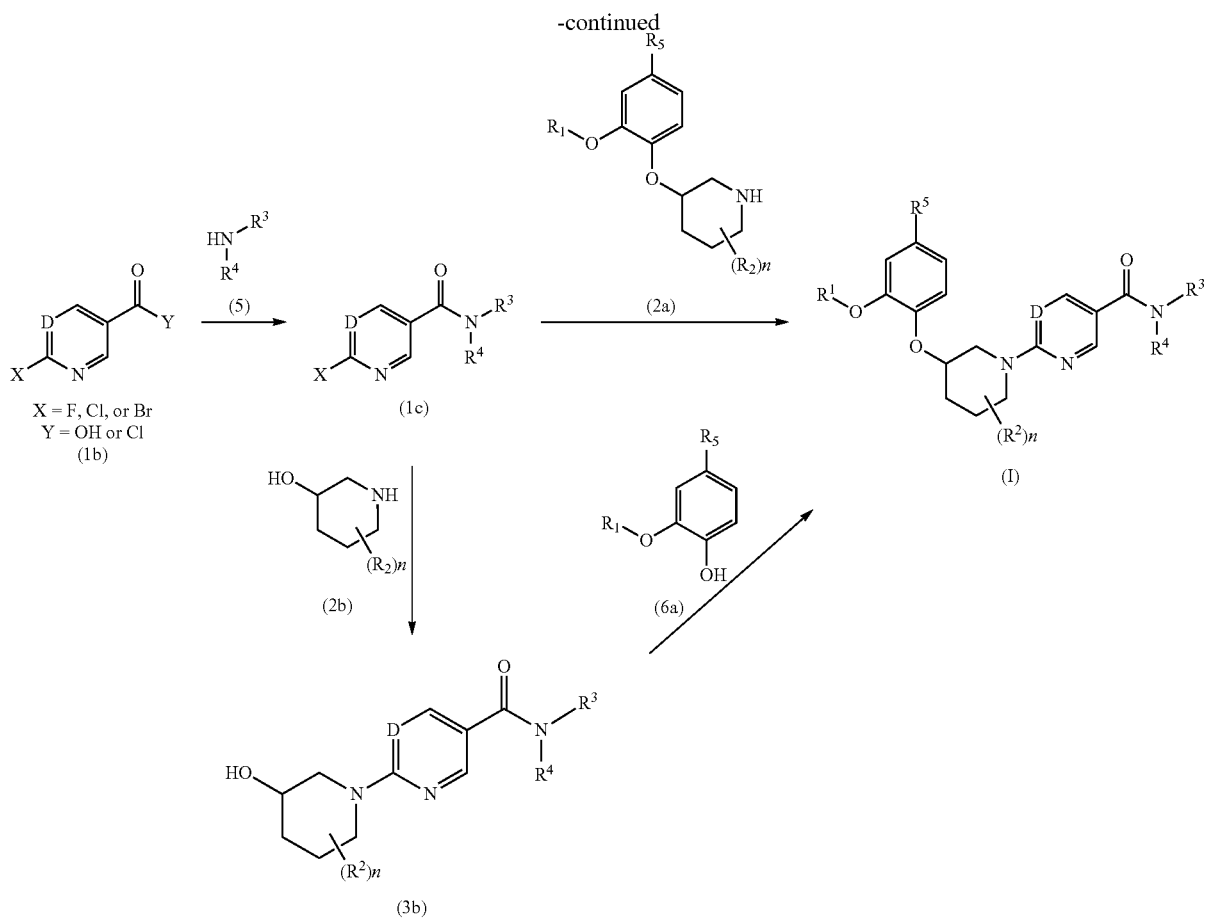

Compounds of Formula (I) may be synthesized starting from appropriate intermediates through methods described in the literature such as: *Eur. J. Org. Chem.* 2004, 2763; *Chem. Rev.* 2009, 109, 2551; *Rec. Res. Dev. Org. Chem.* 1997, 1, 273; *Org. React.* 1992, 42, 335; *Angew. Chem. Int. Ed.* 2011, 50, 9943; *J. Am. Chem. Soc.* 2005, 127, 8146; *J. Org. Chem.* 2008, 73, 284; *Org. Lett.* 2002, 4, 973; *Metal Catalyzed Cross-Coupling Reactions and More.* Wiley-VCH, Weinheim, Germany, 2014, 3, 995; *Applications of Transition Metal Catalysis in Drug Discovery and Development*, John Wiley & Sons, Inc., Hoboken, N.J., USA, 2012, 3, 97. Starting materials (1a) and (1b) are commercially available and/or may be prepared via methods known to those skilled in the art. For example, intermediates (1a) and (1b) may be synthesized through methods described in the literature such as: *J. Med. Chem.* 2000, 43, 3995; *Org. Proc. Res. Dev.* 2010, 14, 936. Starting materials (2a) are commercially available or are described in the literature and may be prepared via methods known to those skilled in the art, including those described below (Reaction Scheme III).

Intermediate (3a) may be prepared from heteroaryl halide (1a) in a nucleophilic aromatic substitution reaction by amine (2a) in a reaction inert solvent such as dimethylsulfoxide (DMSO), N,N-dimethylformamide (DMF), acetonitrile, or tetrahydrofuran (THF), in the presence of a suitable base, such as triethylamine (TEA) or N,N-diisopropylethylamine (DIPEA) at a temperature between 10° C. and 120° C. Preferably, intermediates (1a) and (2a) are reacted in DMSO, THF, or acetonitrile in the presence of triethylamine or N,N-diisopropylethylamine, at a temperature between 20° C. and 100° C. Alternatively, intermediate (3a) may be prepared from heteroaryl halide (1a) and amine (2a) via a metal-catalyzed coupling reaction, for example, using a palladium or nickel catalyst, in a reaction inert solvent such as toluene, 1,2-dimethoxyethane, dioxane, DMSO, DMF, or THF, in the presence of a suitable ligand, and a base such as sodium, potassium, or lithium tert-butoxide, or cesium carbonate, at a temperature between 20° C. and 130° C.

Intermediate (4) may be prepared from ester (3a) via a hydrolysis reaction under conditions well known to those skilled in the art. Preferably, intermediate (3a, R=methyl or ethyl) is treated with an aqueous base such as sodium hydroxide, lithium hydroxide, or potassium hydroxide, in a suitable solvent or solvent mixture comprised of water, methanol, and/or THF, at a temperature between 20° C. and 60° C.

Compounds of Formula (I) may be prepared from acid (4) and amine (5) under amide forming conditions well known to those skilled in the art, using coupling reagents such as propane phosphonic acid anhydride ($T_3P$), 1,1'-carbonyldiimidazole (CDI), benzotriazo-1-yloxytris(dimethylamino) phosphonium hexafluorophosphate (BOP), 2-(1H-7-azabenzotriazol-1-yl)-1,1,3,3-tetramethyl uronium hexafluorophosphate methanaminium (HATU), O-benzotriazol-1-yl-N,N,N',N'-tetramethyluronium hexafluoro phosphate (HBTU), 2-chloro-1,3-dimethylimidazolinium chloride (DMC), N-(3-dimethylaminopropyl)-N'-ethylcarbodiimide (EDCI) or 1-hydroxybenzotriazole (HOBT) in a reaction inert solvent such as dichloromethane (DCM), DMF, DMSO, or THF in the presence of a base such as triethylamine, N-methyl-morpholine, or N,N-diisopropylethylamine at a temperature between 10° C. and 90° C., preferably between 20° C. and 65° C.

Alternatively, compounds of Formula (I) may be prepared by a two-step sequence from intermediate (1b) and amine (5) via an amide coupling reaction to afford intermediate (1c), followed by a coupling reaction with amine (2a). Preferably, intermediate (1c) is prepared from acid chloride (1b, Y═Cl) and amine (5) in the presence of a base such as triethylamine or N,N-diisopropylethylamine, in a reaction inert solvent, such as dichloromethane, at a temperature between −20° C. to 30° C., preferably between −20° C. and 0° C. Alternatively, intermediate (1c) may be prepared from acid (1b, Y═OH) and amine (5) in the presence of an amide coupling reagent, such as propane phosphonic acid anhydride ($T_3P$), 1,1'-carbonyldiimidazole (CDI), benzotriazo-1-yloxytris(dimethylamino)phosphonium hexafluorophosphate (BOP), 2-(1H-7-azabenzotriazol-1-yl)-1,1,3,3-tetramethyl uronium hexafluorophosphate methanaminium (HATU), O-benzotriazol-1-yl-N,N,N',N'-tetramethyluronium hexafluoro phosphate (HBTU), 2-chloro-1,3-dimethylimidazolinium chloride (DMC), N-(3-dimethylaminopropyl)-N'-ethylcarbodiimide (EDCI) or 1-hydroxybenzotriazole (HOBT) in a reaction inert solvent such as dichloromethane, DMF, DMSO, or THF in the presence of a base such as triethylamine, N-methyl-morpholine, or N,N-diisopropylethylamine at a temperature between 10° C. and 90° C.

Alternatively, compounds of Formula (I) may be prepared from intermediate (1c) by a two-step sequence involving addition of amine (2b) followed by addition of phenol (6a). Intermediate (3b) may be prepared from heteroaryl halide (1c) and amine (2b) via nucleophilic aromatic substitution in a reaction inert solvent such as DMSO, DMF, acetonitrile, or THF, in the presence of a suitable base, such as triethylamine or N,N-diisopropylethylamine at a temperature between 10° C. and 120° C. Preferably, intermediates (1c) and (2b) are reacted in DMSO, THF, or acetonitrile in the presence of triethylamine or N,N-diisopropylethylamine, at a temperature preferably between 20° C. and 80° C. Alternatively, intermediate (3b) may be prepared from heteroaryl halide (1c) and amine (2b) via a metal-catalyzed coupling reaction, for example, using a palladium or nickel catalyst, in a reaction inert solvent such as toluene, 1,2-dimethoxyethane, 1,4-dioxane, DMSO, DMF, or THF, in the presence of a suitable ligand, and a base such as sodium, potassium, or lithium tert-butoxide, or cesium carbonate, at a temperature between 20° C. and 130° C. Compounds of Formula (I) may then be prepared from alcohol (3b) and phenol (6a) using methods described in the literature, such as US20050137226; WO2005030765. Intermediate (3b) and intermediate (6a) may be coupled by treatment with a combination of reagents to activate the alcohol for displacement, such as triphenylphosphine or tributylphosphine and diethylazodicarboxylate (DEAD), di-tert-butylazodicarboxylate (DBAD), diisopropylazodicarboxylate (DIAD), or bis(2-methoxyethyl) (E)-diazene-1,2-dicarboxylate, in the presence of a base such as triethylamine or N,N-diisopropylethylamine, in a reaction inert solvent, such as dichloromethane, THF, or toluene at a temperature between 0° C. and 40° C.

Reaction Scheme II outlines the synthesis of compounds of Formula (Ic), a subset of compounds of Formula (I) in which the $R^4$ group contains a carboxylic acid functional group. Compounds of Formula (Ic) may be prepared from compounds of Formula (Ib) which contain an ester functionality in the $R^4$ group by cleavage of the ester to a carboxylic acid via methods well known to those skilled in the art. Preferably, an alkyl ester (Ib), such as methyl or ethyl ester, is treated with an aqueous base such as sodium hydroxide, lithium hydroxide, or potassium hydroxide, in a suitable solvent or solvent mixture comprised of water, methanol, and/or tetrahydrofuran, at temperatures ranging from 0° C. to 70° C. Alternatively, a tert-butyl ester may be treated with an acid, such as hydrogen chloride, hydrogen bromide, or trifluoroacetic acid (TFA), in a solvent or solvent mixture containing water, dioxane, acetonitrile, ether, and/or dichloromethane to provide the carboxylic acid compounds of Formula (Ic).

Reaction Scheme II

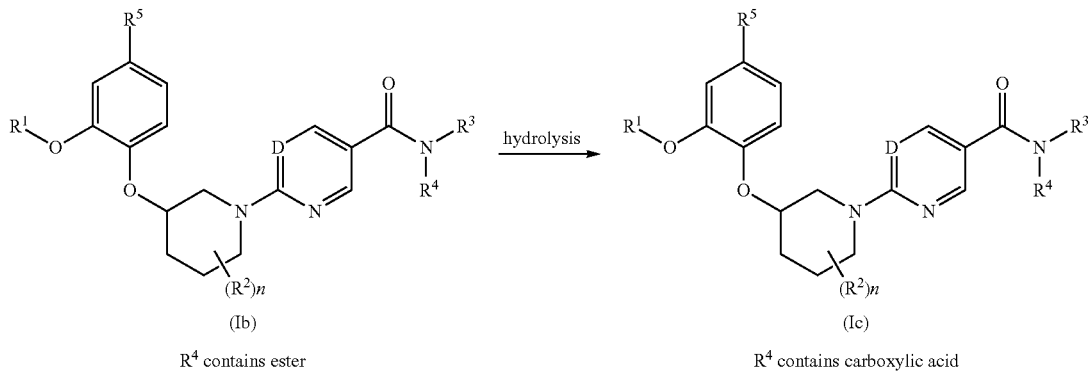

(Ib)
$R^4$ contains ester (Ic)
$R^4$ contains carboxylic acid

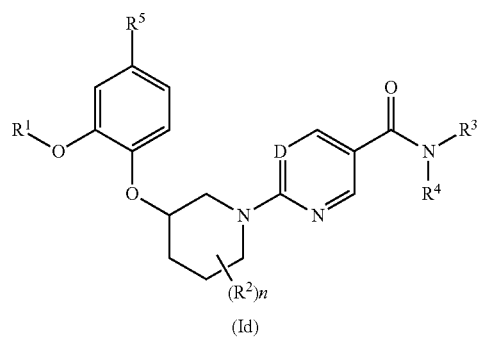

(Id)

R[4] contains aryl or heteroaryl,
substituted with Cl, Br, I, OTf, or OTs

Alternatively, compounds of Formula (Ic) may be prepared from compounds of Formula (Id), in which the R[4] group contains an aryl or heteroaryl ring substituted with a halogen or sulfonate, by methods well known to those skilled in the art, including metal-catalyzed carboxylation reactions or the reaction of an appropriate organometallic species, derived from the halogen, with carbon dioxide or a carbon dioxide equivalent. For example, metal-catalyzed carboxylation may be accomplished using methods described in the literature, such as: *Organomet.* 2008, 27, 5402; *J. Label. Comp. Radiopharm.* 2007, 50, 794; *J. Label. Comp. Radiopharm.* 2000, 43, 1135; *ACS Catalysis* 2013, 3, 2417. A compound of Formula (Id) may be treated with a carbon monoxide source, such as carbon monoxide gas or hexacarbonylmolybdenum(0), in the presence of a metal catalyst, such as tetrakis(triphenylphosphine)palladium(0), palladium(II)acetate, or palladium(II)chloride, and optionally a suitable ligand, in the presence of water, in a solvent such as 1,4-dioxane, tetrahydrofuran, or N,N-dimethylformamide in the presence of appropriate salts or bases, such as tetraethylammonium chloride, tetra-N-propylammonium hydroxide, triethylamine, potassium acetate, or sodium carbonate, at a temperature between 70° C. and 170° C. Preferably, a compound of Formula (Id) containing an aryl-iodide is treated with tetrakis(triphenylphosphine)palladium(0) and carbon monoxide, in the presence of aqueous tetra-N-propylammonium hydroxide in tetrahydrofuran to provide carboxylation product (Ic). Alternatively, a compound of Formula (Id) may be treated with carbon dioxide, in the presence of a catalyst, such as [1,1'-bis(diphenylphosphino)ferrocene]dichloropalladium(II) or copper(I) iodide, and optionally a suitable ligand, in a solvent such as tetrahydrofuran, N,N-dimethylacetamide, or dimethylsulfoxide, in the presence of appropriate salts or bases, such as potassium acetate, at a temperature between 20° C. and 120° C.

Reaction Scheme III outlines the synthesis of intermediates (2a). Reaction Scheme III depicts single enantiomers of intermediates (9), (10), and (2a). Those skilled in the art will recognize that these synthetic routes may be adapted to synthesize either enantiomer, or a racemic mixture of enantiomers, of intermediate (2a).

Reaction Scheme III

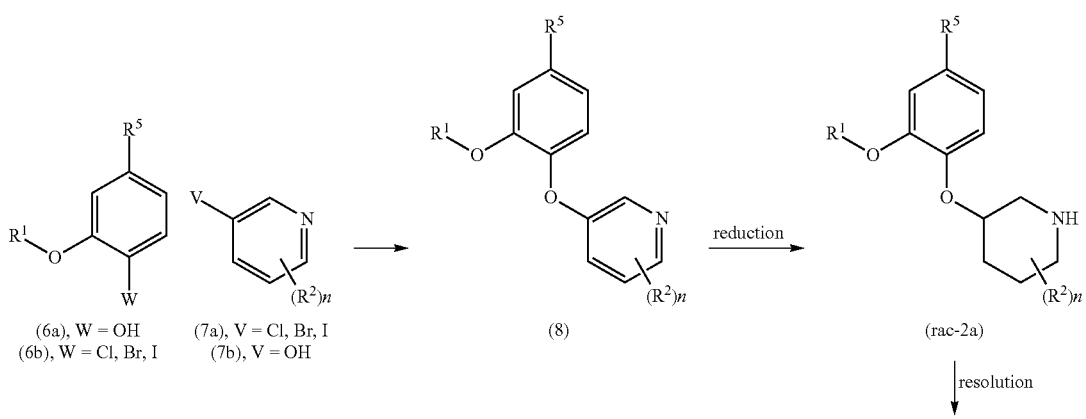

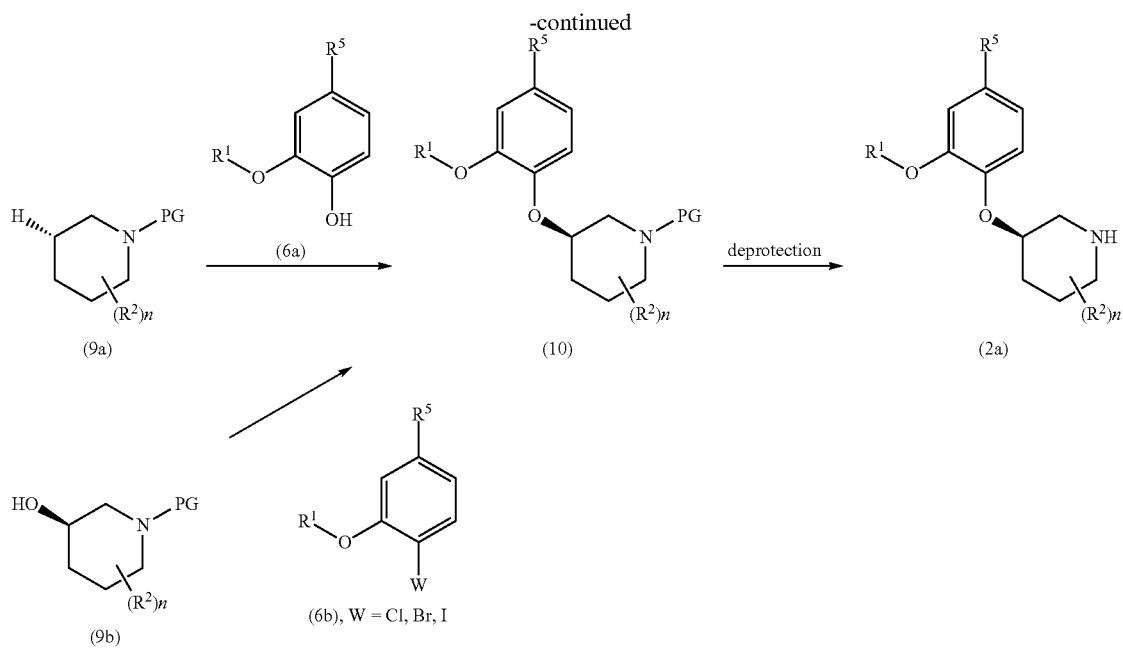

The starting materials (6a), (6b), (7a), and (7b) are commercially available or are described in the literature and may prepared via methods known to those skilled in the art. Intermediate (8) may be synthesized by ether formation between a hydroxy-aromatic coupling partner and an aromatic halide [(6a) and (7a), or (7b) and (6b)] using methods such as those described in: Synlett 2012, 23, 101; J. Org. Chem. 2009, 74, 7187; Org. Lett. 2007, 9, 643. The appropriate starting materials (6) and (7) may be treated with a metal salt, such as copper(I) chloride, copper(I)bromide, or copper(I) iodide, and a ligand such as 2,2,6,6-tetramethyl-heptane-3,5-dione,1,10-phenanthroline, or other suitable ligand, in a reaction inert solvent such as toluene, DMSO, or DMF, in the presence of a base such as potassium carbonate, cesium carbonate, or potassium phosphate, at a temperature of 80° C. to 120° C. Preferably, the appropriate starting materials (6) and (7) are treated with copper(I) chloride and 2,2,6,6-tetramethylheptane-3,5-dione, in toluene, in the presence cesium carbonate, at a temperature of 100° C. to 120° C.

Racemic amine (rac-2a) may be synthesized by reduction of pyridine (8), using methods such as those described in: EP2179988; WO2008140090; Org. Proc. Res. Dev. 2011, 15, 831. For example, intermediate (8) may be treated with a catalyst such as palladium on carbon, rhodium on alumina, or platinum(IV) oxide, in the presence of a reducing agent such as hydrogen gas, in a solvent such as acetic acid, methanol, or ethanol, optionally in the presence of an acid, such as acetic acid or hydrogen chloride. Preferably, intermediate (8) is reduced with hydrogen gas and rhodium on alumina, in the presence of hydrochloric acid, in methanol or ethanol, at a temperature of 40° C. to 60° C.

Intermediate (2a), stereochemically enriched in one enantiomer, may be prepared from racemic intermediate (rac-2a) using methods known to those skilled in the art, such as chiral chromatography, as described in: Biopharm. Drug Dispos. 2001, 22, 291; Ann. Rev. Anal. Chem. 2010, 3, 341; Org. Proc. Res. Dev. 2011, 15, 831; or diastereomeric salt resolution, as described in: Cryst. Growth Des. 2011, 11, 3761; Org. Proc. Res. Dev. 2011, 15, 831; Tetr.: Asymm. 2012, 23, 221; Tetr.: Asymm. 2006, 17, 1337. Preferably, intermediate (rac-2a) is treated with a chiral acid, such as D-tartaric acid, in a reaction inert solvent, such as acetone, at an appropriate temperature to induce selective crystallization of a diastereomeric salt complex of intermediate (2a).

Alternatively, stereochemically enriched intermediate (2a) may be prepared from stereochemically enriched intermediate (9a) by a two-step sequence. Intermediate (10) may be prepared from alcohol (9a) and phenol (6a) using methods described in the literature, such as US20050137226; WO2005030765. Intermediate (9a) and intermediate (6a) may be coupled by treatment with a combination of reagents to activate the alcohol for displacement, such as triphenylphosphine or tributylphosphine and diethylazodicarboxylate, di-tert-butylazodicarboxylate, diisopropylazodicarboxylate, or bis(2-methoxyethyl) (E)-diazene-1,2-dicarboxylate, optionally in the presence of a base such as triethylamine or N,N-diisopropylethylamine, in a reaction inert solvent, such as dichloromethane, THF, or toluene at a temperature between 0° C. and 40° C. Preferably, the amine protecting group (PG) is a carbamate, such as tert-butyl carbamate (Boc). Intermediate (2a) may then be prepared by removal of the protecting group (PG), which is well known to those skilled in the art. For a general description of protecting groups and their use, see T. W. Greene, Protective Groups in Organic Synthesis, John Wiley & Sons, New York, 1991. When PG=Boc, the deprotection conditions preferably involve treatment of intermediate (10) with acid, such as hydrogen chloride or trifluoroacetic acid, in a reaction inert solvent, such as dichloromethane or dioxane, at a temperature of 20° C. to 40° C.

Alternatively, intermediate (2a) may be prepared from intermediate (9b) by a two-step sequence. Alcohol (9b) and halide (6b) may be coupled using methods described in US20050137226; Angew. Chem. Int. Ed. 2011, 50, 9943; J. Am. Chem. Soc. 2005, 127, 8146; J. Org. Chem. 2008, 73, 284; Org. Lett. 2002, 4, 973. Alcohol (9b) and halide (6b) may be treated with a metal salt, such as copper(I) chloride, copper(I) bromide, copper(I) iodide, palladium(II) acetate, or allylpalladium(II) chloride dimer, and a ligand, such as 1,10-phenanthroline, or other suitable ligand, in a reaction inert solvent such as toluene, DMSO, or DMF, in the presence of a base such as cesium carbonate, at a temperature of 70° C. to 120° C.

Reaction Scheme IV outlines the synthesis of amines (5a), a subset of the amines (5) illustrated in Reaction Scheme I. Intermediates (11), (12), and (13) are commercially available or are reported in the literature and may prepared via methods known to those skilled in the art. For example, intermediate (11) may be synthesized using methods described in the literature such as: *Chem. Eur. J.* 2012, 18, 2978; *Synlett* 2003, 2237; *Tetr.* 2005, 61, 9908; WO2010100050. Intermediates (12) and (13) may be synthesized using methods described in the literature such as: *J. Am. Chem. Soc.* 1999, 121, 10286; *Chem Bio Chem* 2007, 8, 68; *J. Med. Chem.* 2011, 54, 4350; WO2010036632. Intermediate (5a) may be prepared from intermediate (11) by reduction, using methods such as those described in: *Chem. Eur. J.* 2005, 11, 5674; *Bioorg. Med. Chem.* 2013, 21, 2056; *J. Med. Chem.* 2004, 47, 5501; *J. Med. Chem.* 2005, 48, 664. For example, intermediate (11) may be treated with a reducing agent, such as hydrogen gas, in the presence of a metal catalyst, such as Raney nickel or palladium on carbon, in an appropriate solvent, such as methanol or ethanol, at a temperature of 20° C. to 60° C. Alternatively, intermediate (11) may be treated with a reducing agent-metal salt combination, such as sodium borohydride and nickel(II) chloride, in an appropriate solvent, such as methanol or tetrahydrofuran, at a temperature of 0° C. to 40° C. Preferably, intermediate (11) is treated with palladium on carbon and hydrogen gas, in methanol or ethanol, at a temperature of 20° C. to 40° C.

Reaction Scheme IV

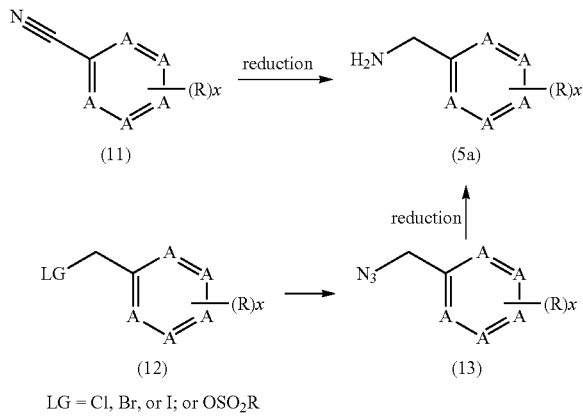

LG = Cl, Br, or I; or OSO$_2$R
x = 0, 1, 2, 3 or 4
A = CH, CR or N
R = Substituents of R$^4$ described in the summary Alternatively, intermediate (5a) may be prepared from intermediate (13) using methods such as those described in: *J. Org. Chem.* 2006, 71, 7205; *J. Org. Chem.* 2009, 74, 895; WO2005021532; WO2005111003; US 20100009954. For example, intermediate (13) may be treated with a reducing agent, such as hydrogen gas, in the presence of a metal catalyst, such as platinum on carbon or palladium on carbon, in an appropriate solvent, such as methanol, ethanol, or ethyl acetate at a temperature of 20° C. to 60° C. Alternatively, intermediate (13) may be treated with a reducing agent such as lithium aluminum hydride, in an appropriate solvent, such as tetrahydrofuran or diethyl ether, at a temperature of 0° C. to 40° C. Alternatively, intermediate (13) may be treated with a reducing agent such as triphenylphosphine or tributylphosphine, in the presence of water, and in an appropriate solvent such as tetrahydrofuran, at a temperature of 20° C. to 40° C. Preferably, intermediate (13) is prepared by treatment of intermediate (12), which contains a leaving group such as chloride, bromide, iodide, methanesulfonate, or 4-toluenesulfonate, with sodium azide in a reaction inert solvent such as methanol, at a temperature of 20° C. to 70° C., and intermediate (13) is reduced with hydrogen gas and palladium on carbon in methanol or ethanol, at a temperature of 20° C. to 40° C.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition e.g., obesity, diabetes, and cardiovascular conditions such as anti-hypertensive agents and coronary heart disease.

Examples of suitable anti-diabetic agents include (e.g. insulins, metfomin, DPPIV inhibitors, GLP-1 agonists, analogues and mimetics, SGLT1 and SGLT2 inhibitors). Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., *Drug*

*Discovery Today*, 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), Ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buprorion and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), the combination of naltrexone with buprorion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3), phentermine and topiramate (trade name: Qsymia), and sibutramine. Preferably, compounds of the present invention and combination therapies are administered in conjunction with exercise and a sensible diet.

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants (such as questran); ACAT inhibitors; MTP inhibitors; lipooxygenase inhibitors; choesterol absorption inhibitors; and cholesteryl ester transfer protein inhibitors. Other atherosclerotic agents include PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buprorion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I or Ia may be co-administered with furosemide. In still another embodiment, one or more compounds of Formula I or Ia may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I or Ia may be co-administered with chlorothiazide. In still another embodiment, one or more compounds of Formula I or Ia may be co-administered with hydrochlorothiazide.

In another embodiment, one or more compounds of Formula I or Ia may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-obesity agent,) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

According to the methods of the invention, a compound of the present invention or a combination is preferably administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1.mu.g/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456, 923 and 5,939,099, which describe forming dispersions by extrusion processes; U.S. Pat. Nos. 5,340,591 and 4,673, 564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt 10 wt %, 25 wt 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.®-LF, Aqoat.sup.®-MF and Aqoat-.sup.®-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about 10.sub.-3 to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), BOP (benzotriazo-1-yloxytris (dimethylamino)phosphonium hexafluorophosphate), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N'-dimethylformamide), DMSO (dimethylsulfoxide), EDCI (N-(3-dimethylaminopropyl)-N'-ethylcarbodiimide), $Et_2O$ (diethyl ether), EtOAc (ethyl acetate), EtOH (ethanol), HATU (2-(1H-7-azabenzotriazol-1-yl)-1,1,3,3-tetramethyl uronium hexafluorophosphate methanaminium), HBTU (O-benzotriazol-1-yl-N,N,N',N'-tetramethyluronium hexafluoro phosphate), HOBT (1-hydroxybenzotriazole), IPA (isopropyl alcohol), KHMDS (potassium hexamethyldisilazane), MeOH (methanol), MTBE (tert-butyl methyl ether), $NaBH(OAc)_3$ (sodium triacetoxyborohydride), NaHMDS (sodium hexamethyldisilazane), NMP (N-methylpyrrolidone), SEM ([2-(Trimethylsilyl) ethoxy]methyl), TEA (triethylamine), TFA (trifluoroacetic acid), THF (tetrahydrofuran), and $T_3P$ (propane phosphonic acid anhydride).

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. Commercial solvents and reagents were used without further purification. When indicated, reactions were heated by microwave irradiation using Biotage Initiator or Personal Chemistry Emrys Optimizer microwaves. Reaction progress was monitored using thin layer chromatography (TLC), liquid chromatography-mass spectrometry (LCMS), high performance liquid chromatography (HPLC), and/or gas chromatography-mass spectrometry (GCMS) analyses. TLC was performed on pre-coated silica gel plates with a fluorescence indicator (254 nm exitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy CH NMR) chemical shifts are given in parts per million downfield from tetramethylsilane and were recorded on 300, 400, 500, or 600 MHz Varian spectrometers. Chemical shifts are expressed in parts per million (ppm, δ) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

The compounds and intermediates described below were named using the naming convention provided with ChemBioDraw Ultra, Version 12.0 (CambridgeSoft Corp., Cambridge, Mass.). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra performance liquid chromatography and "HPLC" refers to high pressure liquid chromatography, "SFC" refers to supercritical fluid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

Preparation of Intermediates and Examples

Intermediate 1. (R)-2-(3-(2-Ethoxyphenoxy)piperidin-1-yl)pyrimidine-5-carboxylic acid

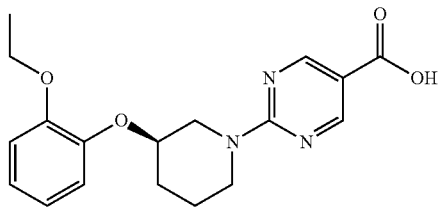 [SMILES: CCOc1ccccc1O[C@@H]1CCCN(c2ncc(C(=O)O)cn2)C1]

Step 1. tert-Butyl (R)-3-(2-ethoxyphenoxy)piperidine-1-carboxylate

To a solution of 2-ethoxyphenol (13.72 g, 99 mmol), tert-butyl (S)-3-hydroxypiperidine-1-carboxylate (20 g, 99 mmol), and triphenylphosphine (29 g, 111 mmol) in toluene (150 mL) at 20-25° C. was added a solution of DIAD (20 mL, 104 mmol) in toluene (50 mL) over 2 hours. After 2 hours, the reaction mixture was filtered and washed with diethyl ether (300 mL). The filtrate was washed with 3N NaOH (150 mL), dried over Na$_2$SO$_4$, and concentrated. The crude residue was purified via column chromatography to afford tert-butyl (R)-3-(2-ethoxyphenoxy)piperidine-1-carboxylate (14.6 g, 45%). MS (ES+) 222.2 (M−100+H).

Step 2. (R)-3-(2-Ethoxyphenoxy)piperidine

To a solution of tert-butyl (R)-3-(2-ethoxyphenoxy)piperidine-1-carboxylate (73 g, 227 mmol) in CH$_2$Cl$_2$ (300 mL) at 20-25° C. was added trifluoroacetic acid (150 mL). The reaction mixture was allowed to stir at 20-25° C. for 4 hours. The mixture was concentrated under reduced pressure, and the residue was dissolved in H$_2$O (200 mL) and basified with saturated NaHCO$_3$ solution (200 mL). The mixture was extracted with EtOAc (3 times with 200 mL). The organic extracts were dried over Na$_2$SO$_4$ and concentrated to afford (R)-3-(2-ethoxyphenoxy)piperidine (45 g, 89%). MS (ES+) 222.2 (M+H).

Step 3. Ethyl (R)-2-(3-(2-ethoxyphenoxy)piperidin-1-yl)pyrimidine-5-carboxylate

To a solution of (R)-3-(2-ethoxyphenoxy)piperidine (45 g, 204 mmol) and ethyl 2-chloropyrimidine-5-carboxylate (41.7 g, 224 mmol) in DMSO (300 mL) was added Et$_3$N (40 mL, 305 mmol) at 20-25° C. The reaction mixture was heated to 100° C. for 2 hours, then was cooled to 20-25° C., diluted with H$_2$O (300 mL) and extracted with EtOAc (3 times with 300 mL). The combined organic extracts were dried over Na$_2$SO$_4$, filtered, and concentrated to obtain ethyl (R)-2-(3-(2-ethoxyphenoxy)piperidin-1-yl)pyrimidine-5-carboxylate (71.5 g). MS (ES+) 372.3 (M+H).

Step 4. (R)-2-(3-(2-Ethoxyphenoxy)piperidin-1-yl)pyrimidine-5-carboxylic acid

To a solution of ethyl (R)-2-(3-(2-ethoxyphenoxy)piperidin-1-yl)pyrimidine-5-carboxylate (71.5 g, 193 mmol) in THF/H$_2$O (1:1, 2 L) was added LiOH.H$_2$O (24.2 g, 578 mmol) at 20-25° C. The reaction mixture was stirred at 20-25° C. for 24 hours. The mixture was concentrated, and the aqueous phase was washed with diethyl ether (2 times with 500 mL). The aqueous phase was acidified to pH 2 with 1N HCl (~400 mL). The precipitated solid was filtered and dried to afford (R)-2-(3-(2-ethoxyphenoxy)piperidin-1-yl)pyrimidine-5-carboxylic acid (52 g, 78%). MS (ES+) 344.18 (M+H).

Intermediate 1, Alternate Procedure. (R)-2-(3-(2-Ethoxyphenoxy)piperidin-1-yl)pyrimidine-5-carboxylic acid

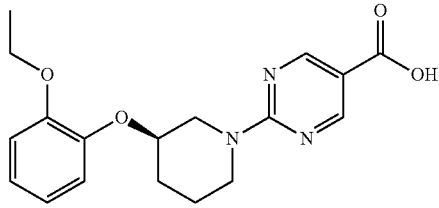 [SMILES: CCOc1ccccc1O[C@@H]1CCCN(c2ncc(C(=O)O)cn2)C1]

Step 1. 3-(2-Ethoxyphenoxy)pyridine

3-Bromopyridine (224 g, 1.42 mol) and 2-ethoxyphenol (275 g, 1.99 mol) were added to a jacketed reactor vessel containing toluene (2.2 L) at 20° C., and the resulting mixture was stirred until all solids were dissolved. 2,2,6,6-Tetramethylheptane-3,5-dione (118 g, 0.640 mol), copper(I) chloride (71.8 g, 0.71 mol), and cesium carbonate (749 g, 2.27 mol) were added sequentially, and the jacket temperature was raised to 119° C. The mixture became thick, and stirring resumed as the temperature increased. After 20 hours, the mixture was cooled to 30° C. The organic layer was washed sequentially with water (0.75 L) and with aqueous 15% ammonium hydroxide solution (0.70 L), and then was extracted with aqueous 3M hydrochloric acid solution (1.18 L, 3.55 mol). Ethyl acetate (1.8 L) and aqueous 15% ammonium hydroxide solution (0.500 L, 3.60 mol) were then added sequentially to the acidic aqueous phase. The blue aqueous layer was separated, and the resulting organic layer was washed sequentially with aqueous 15% ammonium hydroxide solution (0.50 L) and with 2:1 water:brine solution (0.30 L). The organic layer and Darco G60 activated charcoal (60 g) were stirred at 45° C. for 1 hour, and then were filtered through a pad of Celite, rinsing with ethyl acetate (0.35 L). The filtrate was concentrated under vacuum and the resulting residue was re-concentrated from methanol (0.30 L) to afford 3-(2-ethoxyphenoxy)pyridine (233 g) as a yellow oil. $^1$H NMR (400 MHz, DMSO-d$_6$) δ 8.25 (s, 2H), 7.34 (dd, 1H), 7.18 (m, 4H), 6.99 (t, 1H), 4.01 (q, 2H), 1.11 (t, 3H).

Step 2. 3-(2-Ethoxyphenoxy)piperidine hydrochloride

Aqueous 12.2M hydrochloric acid solution (80.0 mL, 0.976 mol) was added slowly to a mixture of 3-(2-ethoxyphenoxy)pyridine (210 g, 0.976 mol), rhodium (5% on alumina, 21 g, 0.010 mol), and methanol (2.1 L) in a Parr reactor. The reactor was purged sequentially with nitrogen and hydrogen (4 times each), and then was heated to 50° C. and pressurized to 50 psi with hydrogen. After 9 hours, the reactor was cooled to 25° C. and was purged with nitrogen. The catalyst was removed by filtration, rinsing with methanol. The resulting methanol solution was distilled to a low volume under reduced pressure at 50-55° C.; ethyl acetate (2.3 L) was added and the distillation was continued at ambient pressure and at constant volume with the addition of further ethyl acetate (1.5 L). The distillation was stopped when the solution became turbid. The mixture was cooled to 20° C. and the resulting crystals were collected by filtration, rinsing with ethyl acetate (0.70 L), to afford after drying 3-(2-ethoxyphenoxy)piperidine hydrochloride (201 g). $^1$H NMR (400 MHz, DMSO-$d_6$) δ 9.20 (br s, 2H), 7.12 (d, 1H), 7.03 (m, 2H), 6.89 (m, 1H), 4.45 (m, 1H), 4.04 (q, 2H), 3.27 (app dd, 1H), 3.05 (m, 3H), 1.94 (m, 2H), 1.72 (m, 2H), 1.35 (t, 3H). MS (ES+) 222.1 (M+H).

Step 3. (R)-3-(2-Ethoxyphenoxy)piperidine D-tartrate

A slurry of 3-(2-ethoxyphenoxy)piperidine hydrochloride (200 g, 0.776 mol) and D-tartaric acid (118 g, 776 mol) in acetone (3.0 L) was warmed to 56° C. and was held at that temperature for 2 hours. The mixture was cooled to 20° C. and was held at that temperature overnight. The crystals were collected by filtration, rinsing with acetone (1 L), and then were dried to afford (R)-3-(2-ethoxyphenoxy)piperidine D-tartrate (145 g). Chiral HPLC analysis indicated an enantiomeric ratio of 99.5:0.5 (Chiralpak AD-H, 4.6×250 mm, 5 μm, 210 nM, 0.2% isopropylamine-isopropanol, 0.7 mL/min; retention times 5.76 min (major enantiomer), 6.20 min (minor enantiomer). $^1$H NMR (400 MHz, DMSO-$d_6$) δ 12.69 (br s, 1.5H), 9.34 (br s, 1H), 8.79 (br s, 1H), 7.12 (d, 1H), 7.03 (m, 2H), 6.89 (m, 1H), 5.09 (br s, 1.5H), 4.44 (m, 1H), 4.32 (s, 2H), 4.05 (q, 2H), 3.28 (m, 1H), 3.11 (m, 1H), 3.04 (m, 2H), 1.97 (m, 1H), 1.92 (m, 1H), 1.72 (m, 2H), 1.35 (s, 3H).

Step 4. (R)-2-(3-(2-Ethoxyphenoxy)piperidin-1-yl)pyrimidine-5-carboxylic acid N,N-Diisopropylethylamine (2.91 kg, 22.5 mol) was added to a mixture of ethyl 2-chloropyrimidine-5-carboxylate (1.20 kg, 6.43 mol) and (R)-3-(2-ethoxyphenoxy)piperidine D-tartrate (2.63 kg, 7.07 mol) in tetrahydrofuran (12.0 L) at 55° C., at a rate maintaining a temperature of 50-60° C. The mixture was held at that temperature for 1 hour, then was cooled to 30° C. The mixture was then partitioned between water (8.4 L) and 2-methyltetrahydrofuran (16.8 L). The organic layer was washed with aqueous 2M sodium chloride solution (6.8 L), and then was concentrated by distillation under reduced pressure. Tetrahydrofuran (12.0 L) and methanol (6.0 L) were added to the residue, and then an aqueous 8M potassium hydroxide solution was added at a rate to maintain the temperature below 55° C. The mixture was held at 50-55° C. for 1 hour, then was cooled to 30° C., and was partitioned between ethyl acetate (18.0 L) and aqueous 3M hydrochloric acid solution (8.86 L). The organic layer was washed with aqueous 2M sodium chloride solution (6.8 L), and was then distilled to a low volume. Ethyl acetate (22 L) was added and the resulting solution was distilled at ambient pressure and at constant volume with the addition of further ethyl acetate (25 L). The mixture was cooled to and held at 57° C. for 2 hours as crystallization initiated. n-Heptane (8.83 L) was added while maintaining temperature at 55-60° C. After 30 min, the slurry was cooled to 20-25° C. and was held at that temperature for 11 hours. The crystals were collected by filtration, rinsing with 2:1 ethyl acetate:n-heptane (8.0 L), to afford after drying (R)-2-(3-(2-ethoxyphenoxy)piperidin-1-yl)pyrimidine-5-carboxylic acid (1.69 kg). MS (ES+) 344.3 (M+H). The mother liquors were concentrated and the resulting residue was recrystallized from ethyl acetate (4.2 L), with the addition of n-heptane (2.1 L) after crystallization initiated, to afford after filtering and drying an additional portion of (R)-2-(3-(2-ethoxyphenoxy)piperidin-1-yl)pyrimidine-5-carboxylic acid (0.370 kg).

Intermediate 2. Methyl 3-(aminomethyl)-5-methoxybenzoate hydrochloride

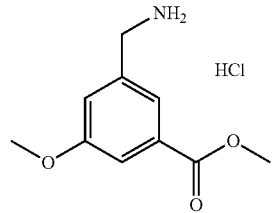

To a solution of methyl 3-cyano-5-methoxybenzoate (280 mg, 1.46 mmol) in MeOH (15 mL) was added 10% Pd/C (150 mg). The mixture was hydrogenated under an atmosphere of $H_2$ for 6 hours. The mixture was filtered through a pad of celite under $N_2$ and the filtrate was added to an ethereal-HCl solution (6 mL). The resultant mixture was evaporated under reduced pressure and the resulting residue was triturated with ethyl acetate to obtain methyl 3-(aminomethyl)-5-methoxybenzoate hydrochloride (120 mg).

Intermediate 2A. Methyl 3-(aminomethyl)-4-methylbenzoate hydrochloride

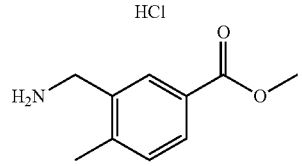

Methyl 3-(aminomethyl)-4-methylbenzoate hydrochloride was prepared from methyl 3-cyano-4-methylbenzoate in an analogous manner to Intermediate 2.

Intermediate 2B. Methyl 3-(aminomethyl)-4-fluorobenzoate hydrochloride

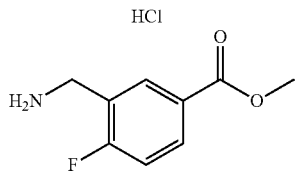

Methyl 3-(aminomethyl)-4-fluorobenzoate hydrochloride was prepared from methyl 3-cyano-4-fluorobenzoate in an analogous manner to Intermediate 2.

Intermediate 2C. Methyl 3-(aminomethyl)-4-methoxybenzoate hydrochloride

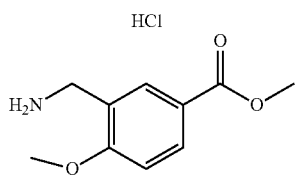

Methyl 3-(aminomethyl)-4-methoxybenzoate hydrochloride was prepared from methyl 3-cyano-4-methoxybenzoate in an analogous manner to Intermediate 2.

Intermediate 2D. Methyl 3-(aminomethyl)-5-methylbenzoate hydrochloride

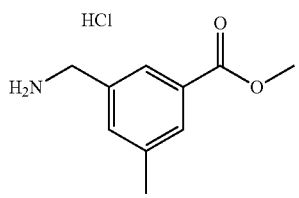

Methyl 3-(aminomethyl)-5-methylbenzoate hydrochloride was prepared from methyl 3-cyano-5-methylbenzoate in an analogous manner to Intermediate 2.

Intermediate 2E. Ethyl 3-(aminomethyl)-2-methoxybenzoate hydrochloride

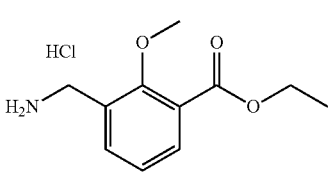

Ethyl 3-(aminomethyl)-2-methoxybenzoate hydrochloride was prepared from ethyl 3-cyano-2-methoxybenzoate in an analogous manner to Intermediate 2.

Intermediate 2F. Ethyl 2-(3-(aminomethyl)phenyl)propanoate hydrochloride

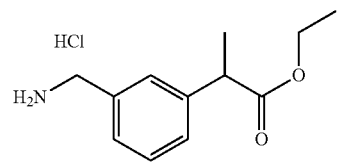

Ethyl 2-(3-(aminomethyl)phenyl)propanoate hydrochloride was prepared from ethyl 2-(3-cyanophenyl)propanoate in an analogous manner to Intermediate 2.

Intermediate 2G. Ethyl 5-(aminomethyl)-6-methylnicotinate hydrochloride

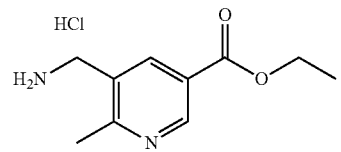

Ethyl 5-(aminomethyl)-6-methylnicotinate was prepared from ethyl 5-cyano-6-methylnicotinate in an analogous manner to Intermediate 2.

Intermediate 3. Methyl 4-(aminomethyl)picolinate

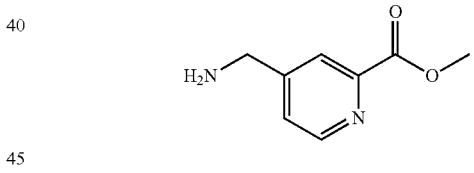

Step 1. Methyl 4-(azidomethyl)picolinate

To solution of methyl 4-(bromomethyl)picolinate (350 mg, 1.52 mmol) in methanol (5 mL) was added a solution of sodium azide (198 mg, 3.04 mmol) in water (0.5 mL). The mixture was heated to reflux for 2 hours, then was concentrated. The resulting residue was dissolved in EtOAc (10 mL) and water (10 mL). The organic layer was separated, dried over $MgSO_4$, filtered and concentrated to give methyl 4-(azidomethyl)picolinate (280 mg).

Step 2. Methyl 4-(aminomethyl)picolinate

To a solution of methyl 4-(azidomethyl)picolinate (280 mg, 1.36 mmol) in methanol (20 mL) was added 10% Pd/C (50 mg). The mixture was stirred under 35 psi $H_2$ for 2 hours. The reaction mixture was filtered through Celite, concentrated, and purified via column chromatography to provide methyl 4-(aminomethyl)picolinate (150 mg).

Intermediate 4: (R)-6-(3-(2-Ethoxyphenoxy)piperidin-1-yl)nicotinic acid

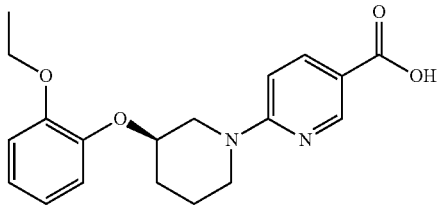

Step 1. Ethyl (R)-6-(3-(2-ethoxyphenoxy)piperidin-1-yl)nicotinate

Triethylamine (8.1 mL, 80 mmol) was added to a stirred solution of (R)-3-(2-ethoxy-phenoxy)-piperidine (10 g, 39 mmol) and ethyl 6-chloronicotinate (7.2 ml, 39 mmol) in acetonitrile (100 mL) at 0° C. The reaction mixture was heated at 90° C. for 16 h. The mixture was cooled to ambient temperature, water (150 mL) was added, and the mixture was extracted with ethyl acetate (3×200 mL). The combined organic layers were washed sequentially with water (100 mL) and brine (100 mL), then were dried over sodium sulfate, filtered and concentrated. The crude material was purified by column chromatography (13% ethyl acetate-hexanes) to afford ethyl (R)-6-(3-(2-ethoxyphenoxy)piperidin-1-yl)nicotinate (8.8 g). MS (ES+) 371.0 (M+H).

Step 2. (R)-6-(3-(2-Ethoxyphenoxy)piperidin-1-yl)nicotinic acid

Aqueous 1N sodium hydroxide solution (27.1 mL, 27.0 mmol) was added to a stirred solution of ethyl (R)-6-(3-(2-ethoxyphenoxy)piperidin-1-yl)nicotinate (2.5 g, 6.8 mmol) in tetrahydrofuran (20 mL) at 0° C. The reaction mixture was heated to 60° C. for 18 h. The mixture was then diluted with water (25 mL) and was washed with ethyl acetate (2×50 mL). The aqueous layer was acidified with citric acid solution (pH-2) and was extracted with ethyl acetate (3×50 mL). The combined organics were dried over sodium sulfate, filtered and concentrated. The crude solid material was purified by washing with ether and hexane to afford (R)-6-(3-(2-ethoxyphenoxy)piperidin-1-yl)nicotinic acid (2.3 g) as white solid. $^1$H NMR (400 MHz, DMSO-d$_6$) δ 12.39 (s, 1H), 8.57 (d, 1H), 7.87 (dd, 1H), 7.03 (dd, 1H), 6.90 (m, 3H), 6.79 (d, 1H), 4.29 (m, 1H), 4.16 (m, 1H), 3.91 (m, 2H), 3.76 (m, 1H), 3.59 (m, 2H), 2.01 (m, 1H), 1.81 (m, 2H), 1.51 (m, 1H), 1.23 (t, 3H). MS (ES+) 343.2 (M+H).

Intermediate 5. (R)-6-(3-(2-Ethoxyphenoxy)piperidin-1-yl)-5-fluoronicotinic acid

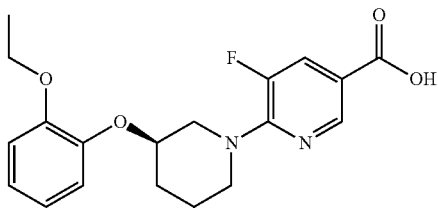 [SMILES: CCOc1ccccc1O[C@@H]1CCCN(c2ncc(C(=O)O)cc2F)C1]

Step 1. Methyl (R)-6-(3-(2-ethoxyphenoxy)piperidin-1-yl)-5-fluoronicotinate

Triethylamine (0.45 mL, 3.3 mmol) was added to a stirred solution of (R)-3-(2-ethoxy-phenoxy)-piperidine (0.41 g, 1.6 mmol) and methyl 6-chloro-5-fluoronicotinate (0.30 g, 1.6 mmol) in acetonitrile (15 mL) at 0° C. The reaction mixture was heated at 50° C. for 18 h. The mixture was cooled to ambient temperature, water (30 mL) was added, and the mixture was extracted with ethyl acetate (3×50 mL). The combined organic layers were dried over sodium sulfate, filtered and concentrated. The crude material was purified by column chromatography (30% ethyl acetate-hexanes) to afford methyl (R)-6-(3-(2-ethoxyphenoxy)piperidin-1-yl)-5-fluoronicotinate (0.40 g). MS (ES+) 375.2 (M+H).

Step 2. (R)-6-(3-(2-Ethoxyphenoxy)piperidin-1-yl)-5-fluoronicotinic acid

Lithium hydroxide hydrate (62 mg, 2.6 mmol) was added to a solution of methyl (R)-6-(3-(2-ethoxyphenoxy)piperidin-1-yl)-5-fluoronicotinate (0.65 g, 1.7 mmol) in tetrahydrofuran (8 mL) and water (8 mL), and the resulting solution was stirred at 20-25° C. for 18 h. The mixture was then diluted with water (20 mL) and was washed with ethyl acetate (2×30 mL). The aqueous layer was acidified with citric acid solution (pH-2) and was extracted with ethyl acetate (3×30 mL). The combined organics were dried over sodium sulfate, filtered, and concentrated to afford (R)-6-(3-(2-ethoxyphenoxy)piperidin-1-yl)-5-fluoronicotinic acid as a white solid (0.50 g). $^1$H NMR (400 MHz, DMSO-d$_6$) δ 12.85 (br s, 1H), 8.46 (s, 1H), 7.68 (dd, 1H), 7.00 (dd, 1H), 6.87 (m, 3H), 4.39 (m, 1H), 4.02 (dd, 1H), 3.89 (m, 2H), 3.68 (m, 3H), 1.97 (m, 2H), 1.79 (m, 1H), 1.55 (m, 1H), 1.22 (t, 3H). MS (ES+) 361.2 (M+H).

Example 1. (R)-3-((2-(3-(2-ethoxyphenoxy)piperidin-1-yl)pyrimidine-5-carboxamido)methyl)benzoic acid

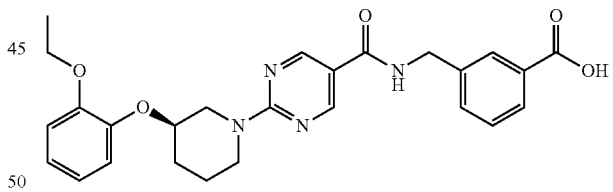

Step 1. (R)-Methyl 3-((2-(3-(2-ethoxyphenoxy)piperidin-1-yl)pyrimidine-5-carboxamido)methyl)benzoate To a 500-mL 3-neck flask was added methyl 3-(aminomethyl)benzoate hydrochloride (12.9 g, 64.1 mmol) followed by DMSO (26 mL). The solution was cooled to 15° C. N-Methyl morpholine (27 mL, 240 mmol) was added followed by EDCI (13 g, 68 mmol) and HOBT (4.09 g, 30 mmol), maintaining the temperature at 15° C. A solution of (R)-2-(3-(2-ethoxyphenoxy)piperidin-1-yl)pyrimidine-5-carboxylic acid (20.94 g, 60.98 mmol) in THF (100 mL) was added dropwise over 10 min. The reaction mixture was warmed to 20-25° C. and stirred for 4 hours. The reaction mixture was concentrated under reduced pressure, and the residue was partitioned between water (200 mL) and pentane-ethyl acetate (1:2, 300 mL). The aqueous phase was further extracted with ethyl acetate (2 times with 100 mL). The combined organic extracts were rinsed sequentially with water (200 mL), saturated aqueous sodium bicarbonate solution (2 times with 100 mL), and brine (2 times with 25 mL). The organic layer was then dried over sodium sulfate, filtered, and concentrated to afford (R)-methyl 3-((2-(3-(2-ethoxyphenoxy)piperidin-1-yl)pyrimidine-5-carboxamido)methyl)benzoate (22.3 g). MS (ES+) 491.3 (M+H).

Step 2. (R)-3-((2-(3-(2-ethoxyphenoxy)piperidin-1-yl)pyrimidine-5-carboxamido)methyl)benzoic acid A solution of (R)-methyl 3-((2-(3-(2-ethoxyphenoxy)piperidin-1-yl)pyrimidine-5-carboxamido)methyl)benzoate (21.3 g, 43.5 mmol) in THF (100 mL) was cooled to 5° C. Aqueous 1.9M lithium hydroxide solution (50 mL, 96 mmol) was added via addition funnel, maintaining the temperature below 14° C., followed by a 30-mL water rinse of the addition funnel. The reaction mixture was warmed to 20-25° C. and was stirred at that temperature for 72 hours. The mixture was concentrated to remove THF, and then was cooled to 8° C. Hydrochloric acid (1N, 80 mL) was added dropwise, and a precipitate began to form. Ethyl acetate (200 mL) was added to dissolve the solids, and the layers were separated, and the aqueous phase was further extracted with ethyl acetate (2 times with 100 mL). The combined organics were washed with brine (4 times with 100 mL), dried over sodium sulfate, filtered, and concentrated under reduced pressure. The crude solid (20.4 g) was slurried in ethanol (250 mL) and heated to 75° C., resulting in a yellow solution. Water (250 mL) was added slowly, forming a precipitate, and the mixture was heated to 90° C. to dissolve the solids. The solution was then cooled to 30° C. and was held at that temperature for 16 hours. The mixture was further cooled to −1.5° C. for 3 hours. The resulting crystals were collected by filtration, rinsed with water (50 mL), and then dried to afford (R)-3-((2-(3-(2-ethoxyphenoxy)piperidin-1-yl)pyrimidine-5-carboxamido)methyl)benzoic acid (19.2 g). $^1$H NMR (500 MHz, CD$_3$OD) δ 8.73 (s, 2H), 8.03 (s, 1H), 7.94 (d, 1H), 7.59 (d, 1H), 7.45 (t, 1H), 7.01 (dd, 1H), 6.92 (m, 1H), 6.86 (m, 1H), 4.60 (s, 2H), 4.37 (m, 1H), 4.14 (dd, 1H), 4.06 (dd, 1H), 3.92 (m, 4H), 2.07 (m, 1H), 1.97 (m, 2H), 1.58 (m, 1H), 1.29 (t, 3H). Chiral SFC: Chiralcel OJ-H, 4.6 mm×25 cm, 70:30 CO$_2$:methanol, 0.2% isopropylamine, 2.5 mL/min, 210/254 nM; retention time (R)-enantiomer (Example 1) 4.13 min, (S)-enantiomer 2.35 min. MS (ES+) 477.3 (M+H).

Example 1, Alternate Procedure. (R)-3-((2-(3-(2-ethoxyphenoxy)piperidin-1-yl)pyrimidine-5-carboxamido)methyl)benzoic acid

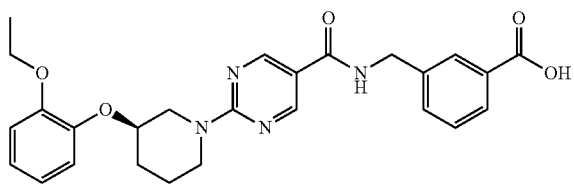

N,N-Diisopropylethylamine (2.32 kg, 17.9 mol) was added via dropping funnel to a mixture of (R)-2-(3-(2-ethoxyphenoxy)piperidin-1-yl)pyrimidine-5-carboxylic acid (2.05 kg, 5.98 mol) and tetrahydrofuran (19.5 L) at 20-25° C. 1,1'-Carbonyldiimidazole (0.94 kg, 5.8 mol) was then added portion-wise, rinsing with tetrahydrofuran (1.03 L), and the mixture was heated to 43-48° C. to dissolve the solids. Methyl 3-(aminomethyl)benzoate hydrochloride (1.39 kg, 6.88 mol) was added, and the reaction mixture was heated to 58-62° C. and was held at that temperature for 3 hours, before being cooled to 20° C. The product mixture was partitioned between aqueous 3M hydrochloric acid solution (8.6 L) and 2-methyltetrahydrofuran (30.8 L). The organic layer was washed sequentially with aqueous 1M hydrochloric acid solution (8.6 L), aqueous 15% ammonium hydroxide solution (2 times with 15 L), and aqueous 2M sodium chloride solution (18 L), and then was concentrated to a low volume under reduced pressure. Methanol (10.27 L) and tetrahydrofuran (20.54 L) were added to the residue and the resulting solution was cooled to 5-10° C. Aqueous 1.5M potassium hydroxide solution (15.9 L, 23.9 mol) was added at a rate maintaining the temperature below 10° C., and the temperature was then held at 15-20° C. for 3 hours. The product mixture was partitioned between aqueous 3M hydrochloric acid solution (8.0 L) and ethyl acetate (30.81 L). The organic layer was washed with aqueous 2M sodium chloride solution (18 L), and then was concentrated under reduced pressure to a volume of approximately 6 L. Ethyl acetate (16.43 L) was added, and the solution was distilled at ambient pressure and at constant volume with the addition of further ethyl acetate (27 L) until the distillation pot temperature was stable at approximately 78° C. The resulting mixture was cooled to 20-25° C. and was held at that temperature for 16 hours. The crystals were collected by filtration, rinsing with ethyl acetate (6.16 L), and then were dried to afford (R)-3-((2-(3-(2-ethoxyphenoxy)piperidin-1-yl)pyrimidine-5-carboxamido)methyl)benzoic acid (2.27 kg). $^1$H NMR (600 MHz, DMSO-d$_6$) δ 12.93 (s, 1H), 8.93 (t, 1H), 8.76 (br s, 2H), 7.89 (s, 1H), 7.82 (d, 1H), 7.54 (d, 1H), 7.44 (t, 1H), 7.01 (d, 1H), 6.89 (m, 2H), 6.84 (m, 1H), 4.50 (d, 2H), 4.29 (m, 1H), 4.14 (dd, 1H), 3.86 (m, 4H), 3.78 (m, 1H), 1.98 (m, 1H), 1.81 (m, 2H), 1.49 (m, 1H), 1.18 (t, 3H). Melting point 151-152° C. Elemental analysis for $C_{26}H_{28}N_4O_5$: calculated C, 65.53; H, 5.92; N, 11.76; found C, 65.41; H, 5.58; N, 11.83.

Powder X-Ray Diffraction Analysis:

The powder X-ray diffraction patterns of the example 1 compound was carried out on a Bruker AXS D4 Endeavor diffractometer using copper radiation (wavelength: 1.54056A). The tube voltage and amperage were set to 40 kV and 40 mA, respectively. The divergence slit was set at 0.6 mm while the secondary optics used variable slits. Diffracted radiation was detected by a PSD-Lynx Eye detector. Data was collected in the Theta-2Theta goniometer at the Cu wavelength from 3.0 to 50.0 degrees 2-Theta using a step size of 0.009 degrees and a step time of 12.0 seconds. Samples were prepared by placing them in a customized holder and rotated during collection. Data were collected using Bruker DIFFRAC Plus software (Version 2.0) and analysis was performed by EVA diffract plus software. PXRD data file was not processed prior to peak searching. Generally, a threshold value of 1 and a Width value of 0.3 were used to make preliminary peak assignments. The output of automated assignments was visually checked to ensure validity and adjustments manually made if necessary.

To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in XRPD peak positions. A systematic study showed that, using a Shimadzu XRD-6000 in the typical Bragg-Brentano configuration, sample height difference of 1 mm lead to peak shifts as high as 1 °2θ (Chen et al.; *J Pharmaceutical and Biomedical Analysis*, 2001; 26, 63). These shifts can be identified from the X-ray Diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 °2θ.

The powder X-ray diffraction values are generally accurate to within ±0.2 2-theta degrees, due to slight variations of instrument and test conditions.

TABLE 1

X-ray powder diffraction pattern:
Peak list for Crystalline Form of Example 1.

| Angle (2-Theta °) | Relative Intensity* (≥10%) |
|---|---|
| 6.9 | 43 |
| 9.7 | 10 |
| 10.3 | 59 |
| 11.0 | 50 |
| 13.0 | 17 |
| 14.9 | 15 |
| 15.1 | 29 |
| 15.3 | 17 |
| 17.1 | 20 |
| 17.3 | 14 |
| 18.2 | 24 |
| 18.5 | 10 |
| 19.1 | 100 |
| 20.2 | 10 |
| 20.7 | 56 |
| 21.8 | 13 |
| 22.0 | 25 |
| 22.8 | 19 |
| 23.2 | 16 |
| 23.5 | 13 |
| 23.8 | 21 |
| 24.1 | 31 |
| 25.4 | 10 |
| 25.7 | 34 |
| 25.9 | 44 |
| 26.7 | 17 |
| 27.2 | 12 |
| 27.6 | 11 |

TABLE 1-continued

X-ray powder diffraction pattern:
Peak list for Crystalline Form of Example 1.

| Angle (2-Theta °) | Relative Intensity* (≥10%) |
|---|---|
| 30.5 | 12 |
| 31.6 | 18 |

*The relative intensities may change depending on the crystal size and morphology.

Single Crystal X-Ray Analysis.

Single crystal for Xray crystallography analysis of (R)-3-((2-(3-(2-ethoxyphenoxy)piperidin-1-yl)pyrimidine-5-carboxamido)methyl)benzoic acid (Example 1) was obtained by following procedure: A solution of (R)-3-((2-(3-(2-ethoxyphenoxy)piperidin-1-yl)pyrimidine-5-carboxamido)methyl)benzoic acid in ethanol (0.14 M) at 68° C. internal temperature was treated with water to reach a final concentration of 0.074 M. The solution was seeded with crystalline (R)-3-((2-(3-(2-ethoxyphenoxy)piperidin-1-yl)pyrimidine-5-carboxamido)methyl)benzoic acid and then was cooled slowly to 20-25° C. to isolate a single crystal suitable for X-ray diffraction.

Single Crystal data collection was performed on a Bruker APEX diffractometer at room temperature. Data collection consisted of 3 omega scans and low angle and three at high angle; each with 0.5 step. In addition, 2 phi scans were collected to improve the quality of the absorption correction. The structure was solved by direct methods using SHELX software suite in the space group P1. The structure was subsequently refined by the full-matrix least squares method. All non-hydrogen atoms were found and refined using anisotropic displacement parameters. Structure exhibits pseudo inversion center. The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms. A non-stoichiometric water molecule was found in the lattice.

Figure 2:
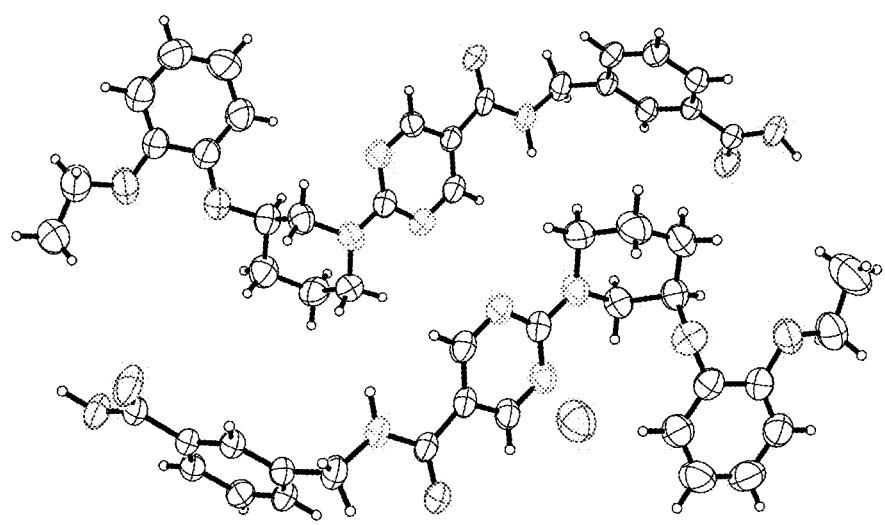
FIG. 2 represents the refined crystal structure for the Example 1 compound which was plotted using the SHELXTL plotting package.

Analysis of the absolute structure using likelihood methods (R. W. W. Hooft et al. J. Appl. Cryst. (2008), 41, 96-103) was performed using PLATON (A. L. Spek, J. Appl. Cryst. (2003), 36, 7-13). The results indicate that the absolute structure has been correctly assigned. The final R-index was 3.9%. A final difference Fourier revealed no missing or misplaced electron density. Pertinent crystal, data collection and refinement of (R)-3-((2-(3-(2-ethoxyphenoxy)piperidin-1-yl)pyrimidine-5-carboxamido)methyl)benzoic acid (Example 1) are summarized in Table 2, and graphically presented in FIG. 2.

TABLE 2

Example 1. Crystal data and structure refinement for Empirical formula C26 H28 N4 O5. 13

| Formula weight | 478.52 | |
|---|---|---|
| Temperature | 273(2) K | |
| Wavelength | 1.54178 Å | |
| Crystal system | Triclinic | |
| Space group | P1 | |
| Unit cell dimensions | a = 9.1042(12) Å | α = 99.787(8)°. |
| | b = 10.8807(14) Å | β = 100.427(8)°. |
| | c = 13.4126(18) Å | γ = 104.796(8)°. |

TABLE 2-continued

Example 1. Crystal data and structure refinement for
Empirical formula C26 H28 N4 O5. 13

| Volume | 1230.3(3) Å3 |
|---|---|
| Z | 2 |

Density (Calculated) 1.292 Mg/m3

Example 1A: [$^{11}$C]—(R)-3-((2-(3-(2-ethoxyphenoxy)piperidin-1-yl)pyrimidine-5-carboxamido)methyl)benzoic acid

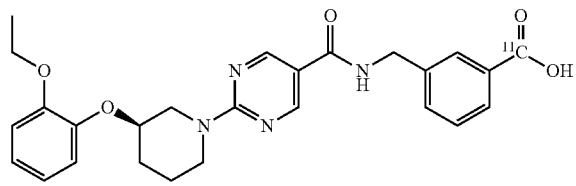 [SMILES: CCOc1ccccc1O[C@@H]1CCCN(c2ncc(C(=O)NCc3cccc([11C](=O)O)c3)cn2)C1]

Step 1. (R)-2-(3-(2-ethoxyphenoxy)piperidin-1-yl)-N-(3-iodobenzyl)pyrimidine-5-carboxamide A mixture of (R)-2-(3-(2-ethoxyphenoxy)piperidin-1-yl)pyrimidine-5-carboxylic acid (2.00 g, 5.82 mmol), (3-iodophenyl)methanamine (1.00 mL, 7.20 mmol), N-methyl morpholine (2.00 mL, 18 mmol), EDCI (1.2 g, 5.9 mmol), and HOBT (455 mg, 2.91 mmol) in THF (30 mL) was stirred at room temperature overnight. The reaction was diluted with EtOAc (50 mL). The organic layer was washed with saturated aqueous solution of NH$_4$Cl (50 mL), saturated aqueous solution of NaHCO$_3$ (50 mL), and brine (50 mL), dried over Na$_2$SO$_4$ and concentrated to dryness. The residue was purified by flash column chromatography (0-50% EtOAc in Heptanes) to afford (R)-2-(3-(2-ethoxyphenoxy)piperidin-1-yl)-N-(3-iodobenzyl)pyrimidine-5-carboxamide (2.39 g, 74%) as a solid. $^1$H NMR (400 MHz, CDCl$_3$) δ 8.69 (s, 2H), 7.69 (m, 1H), 7.64 (m, 1H), 7.32 (m, 1H), 7.10 (t, 1H), 6.98 (m, 2H), 6.88 (m, 2H), 6.13 (t, 1H), 4.58 (d, 2H), 4.48 (dd, 1H), 4.25 (m, 1H), 4.18 (m, 1H), 4.01 (m, 2H), 3.77 (dd, 1H), 3.64 (m, 1H), 2.13 (m, 1H), 1.97 (m, 2H), 1.59 (m, 1H), 1.39 (t, 3H). MS (ES+) 559.2 (M+H).

Step 2. [$^{11}$C]—(R)-3-((2-(3-(2-ethoxyphenoxy)piperidin-1-yl)pyrimidine-5-carboxamido)methyl)benzoic acid Preparation Prior to the Start of Synthesis A clean sequence using tetrahydrofuran (THF) was run on the GE FXc Pro automated CO module prior the start of beam. Prior to beam on, target helium sweep was directed to the CO$_2$ trap in hot cell 1 via the microelectric valve (which allows switching between target delivery to either the CO$_2$ trap or the CO module) for several minutes, then was switched via the microelectric valve to the CO module and the helium gas was swept through the pre-purification unit (PPU) in the CO module for several minutes by having the Vx1 and Vx2 valves in the "active" position. The PPU was then put through a pre-production prep which conditioned and flushed the packing material in the PPU.

[$^{11}$C]CO$_2$ Production

No-carrier-added [$^{11}$C]CO$_2$ was prepared by proton irradiation (30 min, 60 μamp beam) of a 9.5 mL nitrogen gas target [$^{14}$N(p,α)$^{11}$C]. The target was flushed with target gas for 10 minutes, then pressurized to 300 psi and dumped three times before refilling. Two 5 min, 30 μamp pre-burns were performed before the actual beam for the synthesis. Helium was allowed to sweep through the lines and trap in an Ascarite trap in a separate hot cell once beam started (this was switched to the hot cell containing the CO module after 5 min, thus keeping the delivery lines to the CO module pressurized with helium prior to target dump).

Sequence

The Pd(PPh$_3$)$_4$ (stored under nitrogen in the fridge) was warmed to room temperature and weighed out (5.55 mg, 0.005 mmol) in an oven-dried 2 mL septum-sealed vial in an argon glove box, then purged with nitrogen. The precursor, (R)-2-(3-(2-ethoxyphenoxy)piperidin-1-yl)-N-(3-iodobenzyl)pyrimidine-5-carboxamide, was weighed out (5.08 mg, 0.009 mmol) in an oven-dried vial in the open air. Ten minutes before the end of beam, the production sequence for the CO module was started. Both the Pd(PPh$_3$)$_4$ and the precursor were dissolved in 200 μL of anhydrous THF after the vials were purged with nitrogen. The precursor solution was added to the Pd solution under a nitrogen stream (using the THF syringe), and the solution turned from a yellow to a very light yellow. After several minutes the tetra-N-propylammonium hydroxide (50 μL of 1M in water, 0.05 mmol) was added, the contents of the vial shaken, and the same polypropylene syringe was used to remove the solution. The polypropylene syringe was then fitted with a syringe filter (Nalgene 4 mm syringe filter, PTFE, 0.45 μm, cat# F2604-3) and the contents filtered into a separate 2 mL septum-sealed vial that was purging with nitrogen. The filtered solution was then removed with a clean 1 mL polypropylene syringe and loaded into the CO module loop. After the delivery of [$^{11}$C]CO$_2$ to the CO module, the time list for the FXc Pro was started. Following the reaction, 5 minutes at 150° C., the crude mixture was transferred to the reaction vessel of the FXc Pro (via 0.01" ID PEEK line from position 3 of V3 in the CO module to the syringe port of the FXc Pro), and the THF was evaporated at 65° C. in vacuo. The residue was diluted with 0.3 mL dimethylformamide and 1.3 mL 50% acetonitrile/0.1% formic acid, passed through the in-line polypropylene filter, and purified by semi-prep chromatography (Column: Phenomenex Luna C-18(2) 10×250 mm, 5 μm, cat. #00G-4252-N0k; Isocratic: 55% acetonitrile: water with 0.1% formic acid, Flow: 6.0 mL/min; UV: 254 nm) by automated filling of a 2.0 mL Rheodyne loop, followed by injection onto the column. The peak corresponding to [$^{11}$C]—(R)-3-((2-(3-(2-ethoxyphenoxy)piperidin-1-yl)pyrimidine-5-carboxamido)methyl)benzoic acid ($t_R$=8.6 min) was collected and diluted with 50 mL water, followed by trapping on a Waters C8 50 mg vac cartridge (WAT054965). The cartridge was washed with 3.0 mL water, then eluted with ethanol (0.5 mL) and saline (4.5 mL). The final product was analyzed by analytical HPLC. HPLC retention time=8.0 min (Mobile Phase: 50% acetonitrile:0.1% formic acid; Total time of run: 15 min; Flow: 1.0 ml/min; Column: Phenomenex Luna C-18(2), 3 μm, 100 Å, 150×4.6 mm, cat #00F-4251-E0; Detector: UV 280 nm); Synthesis time (from end of beam)=34 min; Specific activity=3965 Ci/mmol; Concentration=16 mCi/mmol; Yield (decay-corrected based on starting amount of crude [$^{11}$C]—(R)-3-((2-(3-(2-ethoxyphenoxy)piperidin-1-yl)pyrimidine-5-carboxamido)methyl)benzoic acid in FXc Pro reactor)=52%; Radiochemical purity=100%; Chemical purity=98.4%.

Example 2. (R)-3-((2-(3-(2-ethoxyphenoxy)piperidin-1-yl)pyrimidine-5-carboxamido)methyl)-5-methoxybenzoic acid

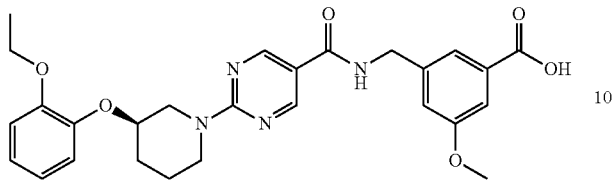

Step 1. Methyl (R)-3-((2-(3-(2-ethoxyphenoxy)piperidin-1-yl)pyrimidine-5-carboxamido)methyl)-5-methoxybenzoate The preparation of methyl (R)-3-((2-(3-(2-ethoxyphenoxy)piperidin-1-yl)pyrimidine-5-carboxamido)methyl)-5-methoxybenzoate serves as a representative procedure referred to as Amidation Method 1 (HATU).

To a suspension of (R)-2-(3-(2-ethoxyphenoxy)piperidin-1-yl)pyrimidine-5-carboxylic acid (50 mg, 0.14 mmol) and HATU (63 mg, 0.17 mmol) in dry dichloromethane (3 mL) was added N,N-diisopropylethylamine (0.075 mL, 0.42 mmol) at 20-25° C. The mixture was stirred for 10 min, then methyl 3-(aminomethyl)-5-methoxybenzoate hydrochloride was added (33 mg, 0.14 mmol) at 20-25° C. The reaction mixture was stirred at 20-25° C. for 1 hour. The mixture was concentrated under reduced pressure and the resulting residue was dissolved in ethyl acetate (10 mL), washed with water (2 times with 10 mL), and dried over $NaSO_4$. The organics were concentrated under reduced pressure to obtain methyl (R)-3-((2-(3-(2-ethoxyphenoxy)piperidin-1-yl)pyrimidine-5-carboxamido)methyl)-5-methoxybenzoate (65 mg, 87%).

Step 2. (R)-3-((2-(3-(2-ethoxyphenoxy)piperidin-1-yl)pyrimidine-5-carboxamido)methyl)-5-methoxybenzoic acid The preparation of (R)-3-((2-(3-(2-ethoxyphenoxy)piperidin-1-yl)pyrimidine-5-carboxamido)methyl)-5-methoxybenzoic acid serves as a representative procedure referred to as Ester Hydrolysis Method 1 (LiOH).

To a solution of methyl (R)-3-((2-(3-(2-ethoxyphenoxy)piperidin-1-yl)pyrimidine-5-carboxamido)methyl)-5-methoxybenzoate (60 mg, 0.11 mmol) in $THF:H_2O$ (1:1, 5 mL) at 20-25° C. was added $LiOH.H_2O$ (15 mg, 0.34 mmol). The mixture was stirred for 18 hours, and then was concentrated under reduced pressure. The resulting residue was diluted with water (5 mL) and washed with ethyl acetate (3 times with 5 mL). The aqueous layer was acidified to pH 2 with 1N HCl (5 mL), and then was extracted with ethyl acetate (3 times with 5 mL). The combined organic extracts were dried over $Na_2SO_4$ and concentrated under reduced pressure to afford (R)-3-((2-(3-(2-ethoxyphenoxy)piperidin-1-yl)pyrimidine-5-carboxamido)methyl)-5-methoxybenzoic acid (40 mg, 72%). $^1H$ NMR (300 MHz, DMSO-$d_6$) δ 8.91 (m, 1H), 8.78 (s, 2H), 7.49 (s, 1H), 7.34 (s, 1H), 7.02 (m, 2H), 6.89 (m, 3H), 4.45 (d, 2H), 4.32 (m, 1H), 4.20 (d, 1H), 3.91 (m, 5H), 3.78 (s, 3H), 2.05 (m, 1H), 1.85 (m, 2H), 1.52 (m, 1H), 1.21 (t, 3H). MS (ES+) 507.1 (M+H).

Example 3. 3-((R)-1-(2-((R)-3-(2-ethoxyphenoxy)piperidin-1-yl)pyrimidine-5-carboxamido)ethyl)benzoic acid

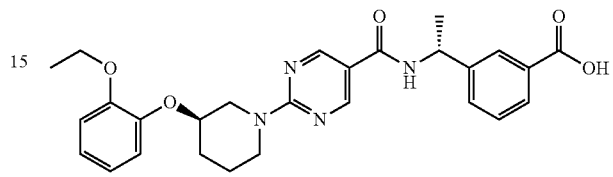

Step 1. Methyl 3-((R)-1-(2-((R)-3-(2-ethoxyphenoxy)piperidin-1-yl)pyrimidine-5-carboxamido)ethyl)benzoate The preparation of methyl 3-((R)-1-(2-((R)-3-(2-ethoxyphenoxy)piperidin-1-yl)pyrimidine-5-carboxamido)ethyl)benzoate serves as a representative procedure referred to as Amidation Method 2 (EDCI).

To a stirred solution of (R)-2-(3-(2-ethoxyphenoxy)piperidin-1-yl)pyrimidine-5-carboxylic acid (797 mg, 2.32 mmol) in dry DMF (2.5 mL) at 0° C. were added triethylamine (0.36 mL, 2.5 mmol), 1-hydroxybenzotriazole (470 mg, 3.48 mmol), and 1-(3-dimethylaminopropyl)-3-ethylcarbodiimide hydrochloride (1666 mg, 3.48 mmol). The mixture was stirred for 5 min and methyl (R)-3-(1-aminoethyl)benzoate (500 mg, 2.32 mmol) was added. The reaction mixture was allowed to warm to 20-25° C. and was stirred for 16 hours. The mixture was poured into water (20 mL) and extracted with ethyl acetate (3 times with 25 mL). The combined organic layers were washed with brine, dried over $Na_2SO_4$, filtered and concentrated. The crude residue was purified via column chromatography to afford methyl 3-((R)-1-(2-((R)-3-(2-ethoxyphenoxy)piperidin-1-yl)pyrimidine-5-carboxamido)ethyl)benzoate (890 mg, 76%). MS (ES+) 505.2 (M+H).

Step 2. 3-((R)-1-(2-((R)-3-(2-ethoxyphenoxy)piperidin-1-yl)pyrimidine-5-carboxamido)ethyl)benzoic acid 3-((R)-1-(2-((R)-3-(2-ethoxyphenoxy)piperidin-1-yl)pyrimidine-5-carboxamido)ethyl)benzoic acid was prepared from methyl 3-((R)-1-(2-((R)-3-(2-ethoxyphenoxy)piperidin-1-yl)pyrimidine-5-carboxamido)ethyl)benzoate using Ester Hydrolysis Method 1 (LiOH). $^1H$ NMR (400 MHz, DMSO-$d_6$) δ 12.9 (br s, 1H), 8.76 (s, 2H), 8.70 (d, 1H), 7.96 (s, 1H), 7.81 (d, 1H), 7.61 (d, 1H), 7.45 (dd, 1H), 7.03 (d, 1H), 6.89 (m, 3H), 5.18 (m, 1H), 4.30 (m, 1H), 4.19 (dd, 1H), 3.89 (m, 4H), 3.77 (m, 1H), 2.01 (m, 1H), 1.83 (m, 2H), 1.51 (m, 1H), 1.46 (d, 3H), 1.21 (t, 3H). MS (ES+) 491 (M+H).

Example 4. (R)-2-(3-(2-ethoxyphenoxy)piperidin-1-yl)-N-ethylpyrimidine-5-carboxamide

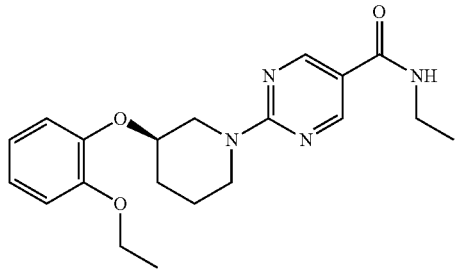 [SMILES: CCNC(=O)c1cnc(N2CCC[C@@H](Oc3ccccc3OCC)C2)nc1]

(R)-2-(3-(2-ethoxyphenoxy)piperidin-1-yl)-N-ethylpyrimidine-5-carboxamide was prepared from (R)-2-(3-(2-ethoxyphenoxy)piperidin-1-yl)pyrimidine-5-carboxylic acid and ethylamine using Amidation Method 1 (HATU). $^1$H NMR (300 MHz, DMSO-$d_6$) δ 8.72 (s, 2H), 8.29 (app t, 1H), 7.08 (d, 1H), 6.91 (m, 3H), 4.31 (m, 1H), 4.21 (app d, 1H), 3.85 (m, 5H), 3.25 (m, 2H), 2.08 (m, 1H), 1.83 (m, 2H), 1.57 (m, 1H), 1.23 (t, 3H), 1.12 (t, 3H). MS (ES+) 371.1 (M+H).

Example 5. (1R,2S)-2-(6-((R)-3-(2-ethoxyphenoxy)piperidin-1-yl)-5-fluoronicotinamido)cyclopentane-1-carboxylic acid

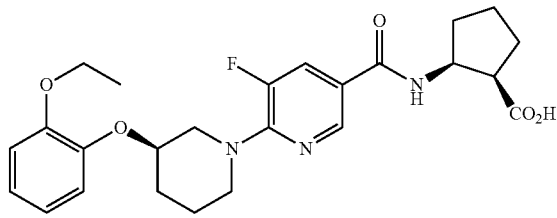 [SMILES: CCOc1ccccc1O[C@@H]1CCCN(c2ncc(C(=O)N[C@H]3CCC[C@H]3C(=O)O)cc2F)C1]

(1R,2S)-2-(6-((R)-3-(2-ethoxyphenoxy)piperidin-1-yl)-5-fluoronicotinamido)cyclopentane-1-carboxylic acid was prepared from (R)-6-(3-(2-ethoxyphenoxy)piperidin-1-yl)-5-fluoronicotinic acid and methyl (1R,2S)-2-aminocyclopentane-1-carboxylate using Amidation Method 2 (EDCI) and Ester Hydrolysis Method 1 (LiOH). $^1$H NMR (400 MHz, DMSO-$d_6$) δ 11.3 (s, 1H), 8.35 (s, 1H), 7.59 (dd, 1H), 7.03 (d, 1H), 6.91 (m, 3H), 4.38 (m, 1H), 4.05 (dd, 1H), 3.93 (m, 3H), 3.69 (m, 1H), 3.50 (m, 2H), 2.33 (m, 1H), 1.98 (m, 4H), 1.79 (m, 1H), 1.60 (m, 3H), 1.45 (m, 2H), 1.25 (t, 3H). MS (ES+) 472.0 (M+H).

Example 6. (1R,2S)-2-(2-((R)-3-(2-ethoxyphenoxy)piperidin-1-yl)pyrimidine-5-carboxamido)cyclopentane-1-carboxylic acid

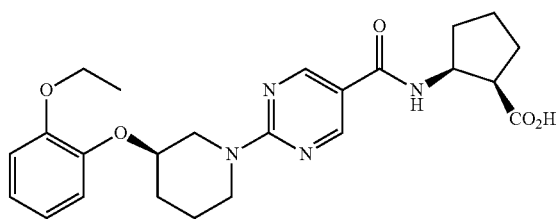 [SMILES: CCOc1ccccc1O[C@@H]1CCCN(c2ncc(C(=O)N[C@H]3CCC[C@H]3C(=O)O)cn2)C1]

(1R,2S)-2-(2-((R)-3-(2-ethoxyphenoxy)piperidin-1-yl)pyrimidine-5-carboxamido)cyclopentane-1-carboxylic acid was prepared from (R)-2-(3-(2-ethoxyphenoxy)piperidin-1-yl)pyrimidine-5-carboxylic acid and methyl (1R,2S)-2-aminocyclopentane-1-carboxylate using Amidation Method 1 (HATU) and Ester Hydrolysis Method 1 (LiOH). $^1$H NMR (400 MHz, DMSO-$d_6$) δ 11.9 (s, 1H), 8.68 (s, 2H), 8.08 (d, 1H), 7.02 (d, 1H), 6.89 (m, 3H), 4.51 (m, 1H), 4.28 (m, 2H), 3.95 (m, 3H), 3.75 (m, 2H), 2.90 (m, 1H), 1.89 (m, 8H), 1.51 (m, 2H), 1.23 (t, 3H). MS (ES+) 455.3 (M+H).

Example 7. (R)-3-((6-(3-(2-ethoxyphenoxy)piperidin-1-yl)nicotinamido)methyl)benzoic acid

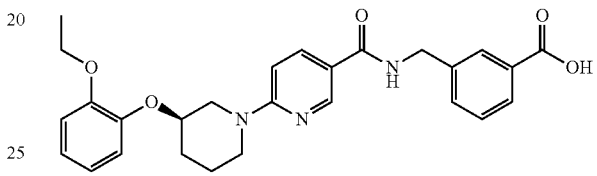

(R)-3-((6-(3-(2-ethoxyphenoxy)piperidin-1-yl)nicotinamido)methyl)benzoic acid was prepared from (R)-6-(3-(2-ethoxyphenoxy)piperidin-1-yl)nicotinic acid and methyl 3-(aminomethyl)benzoate using Amidation Method 1 (HATU) and Ester Hydrolysis Method 1 (LiOH). $^1$H NMR (500 MHz, CD$_3$OD) δ 8.84 (app t, 1H), 8.58 (d, 1H), 8.02 (s, 1H), 7.92 (dd, 2H), 7.58 (d, 1H), 7.44 (t, 1H), 7.01 (d, 1H), 6.92 (m, 2H), 6.87 (m, 1H), 6.73 (d, 1H), 4.60 (m, 2H), 4.37 (m, 1H), 4.05 (dd, 1H), 3.93 (m, 2H), 3.72 (m, 3H), 2.07 (m, 1H), 1.95 (m, 2H), 1.59 (m, 1H), 1.28 (t, 3H). MS (ES+) 476.3 (M+H).

Example 8. (R)-4-((6-(3-(2-ethoxyphenoxy)piperidin-1-yl)-5-fluoronicotinamido)methyl)picolinic acid

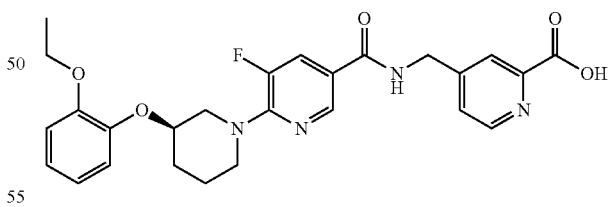

(R)-4-((6-(3-(2-ethoxyphenoxy)piperidin-1-yl)-5-fluoronicotinamido)methyl)picolinic acid was prepared from (R)-6-(3-(2-ethoxyphenoxy)piperidin-1-yl)-5-fluoronicotinic acid and methyl 4-(aminomethyl)picolinate using Amidation Method 2 (EDCI) and Ester Hydrolysis Method 1 (LiOH). $^1$H NMR (500 MHz, CDCl$_3$) δ 8.57 (d, 1H), 8.42 (s, 1H), 8.16 (s, 1H), 7.67 (dd, 1H), 7.57 (d, 1H), 7.03 (dd, 1H), 6.95 (m, 1H), 6.88 (m, 2H), 6.78 (br s, 1H), 4.74 (d, 2H), 4.34 (m, 1H), 4.29 (m, 1H), 4.03 (m, 1H), 3.93 (m, 1H), 3.49 (m, 1H), 3.43 (m, 1H), 2.17 (m, 1H), 2.01 (m, 1H), 1.89 (m, 1H), 1.64 (m, 1H), 1.40 (t, 3H). MS (ES+) 495.2 (M+H).

Example 9. (R)-3-((2-(3-(2-ethoxyphenoxy)piperidin-1-yl)pyrimidine-5-carboxamido)methyl)-4-methylbenzoic acid

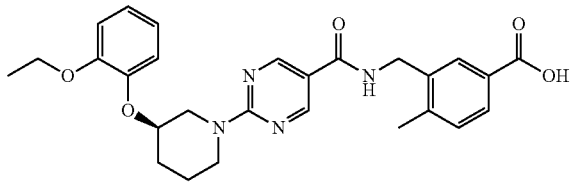 [SMILES: CCOc1ccccc1O[C@@H]1CCCN(c2ncc(C(=O)NCc3cc(C(=O)O)ccc3C)cn2)C1]

(R)-3-((2-(3-(2-ethoxyphenoxy)piperidin-1-yl)pyrimidine-5-carboxamido)methyl)-4-methylbenzoic acid was prepared from (R)-2-(3-(2-ethoxyphenoxy)piperidin-1-yl)pyrimidine-5-carboxylic acid and methyl 3-(aminomethyl)-4-methylbenzoate hydrochloride using Amidation Method 1 (HATU) and Ester Hydrolysis Method 1 (LiOH). $^1$H NMR (400 MHz, DMSO-$d_6$) δ 8.82 (m, 1H), 8.78 (s, 2H), 7.85 (s, 1H), 7.72 (d, 1H), 7.15 (d, 1H), 7.05 (d, 1H), 6.90 (m, 3H), 4.43 (d, 2H), 4.30 (m, 1H), 4.22 (d, 1H), 3.90 (m, 4H), 3.72 (m, 1H), 2.32 (s, 3H), 2.05 (m, 1H), 1.83 (m, 2H), 1.52 (m, 1H), 1.21 (t, 3H). MS (ES+) 491.2 (M+H).

Example 10. (R)-3-((2-(3-(2-ethoxyphenoxy)piperidin-1-yl)pyrimidine-5-carboxamido)methyl)-4-fluorobenzoic acid

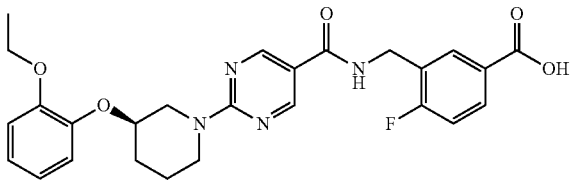 [SMILES: CCOc1ccccc1O[C@@H]1CCCN(c2ncc(C(=O)NCc3cc(C(=O)O)ccc3F)cn2)C1]

(R)-3-((2-(3-(2-ethoxyphenoxy)piperidin-1-yl)pyrimidine-5-carboxamido)methyl)-4-fluorobenzoic acid was prepared from (R)-2-(3-(2-ethoxyphenoxy)piperidin-1-yl)pyrimidine-5-carboxylic acid and methyl 3-(aminomethyl)-4-fluorobenzoate hydrochloride using Amidation Method 1 (HATU) and Ester Hydrolysis Method 1 (LiOH). $^1$H NMR (300 MHz, DMSO-$d_6$) δ 8.92 (m, 1H), 8.78 (s, 2H), 7.91 (d, 1H), 7.85 (m, 1H), 7.19 (dd, 1H), 7.05 (d, 1H), 6.90 (m, 3H), 4.51 (d, 2H), 4.32 (m, 1H), 4.20 (d, 1H), 3.90 (m, 5H), 2.05 (m, 1H), 1.83 (m, 2H), 1.52 (m, 1H), 1.21 (t, 3H). MS (ES+) 495.0 (M+H).

Example 11. (R)-3-((2-(3-(2-ethoxyphenoxy)piperidin-1-yl)pyrimidine-5-carboxamido)methyl)-4-methoxybenzoic acid

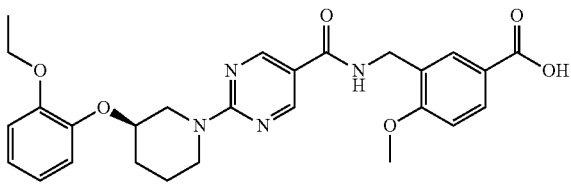 [SMILES: CCOc1ccccc1O[C@@H]1CCCN(c2ncc(C(=O)NCc3cc(C(=O)O)ccc3OC)cn2)C1]

(R)-3-((2-(3-(2-ethoxyphenoxy)piperidin-1-yl)pyrimidine-5-carboxamido)methyl)-4-methoxybenzoic acid was prepared from (R)-2-(3-(2-ethoxyphenoxy)piperidin-1-yl)pyrimidine-5-carboxylic acid and methyl 3-(aminomethyl)-4-methoxybenzoate hydrochloride using Amidation Method 1 (HATU) and Ester Hydrolysis Method 1 (LiOH). $^1$H NMR (300 MHz, DMSO-$d_6$) δ 12.6 (s, 1H), 8.78 (app s, 3H), 7.89 (dd, 1H), 7.76 (m, 1H), 7.10 (d, 1H), 7.05 (d, 1H), 6.89 (m, 3H), 4.45 (d, 2H), 4.38 (m, 1H), 4.18 (d, 1H), 3.91 (m, 8H), 2.05 (m, 1H), 1.88 (m, 2H), 1.52 (m, 1H), 1.21 (t, 3H). MS (ES+) 507.1 (M+H).

Example 12. (R)-5-((2-(3-(2-ethoxyphenoxy)piperidin-1-yl)pyrimidine-5-carboxamido)methyl)-6-methylnicotinic acid

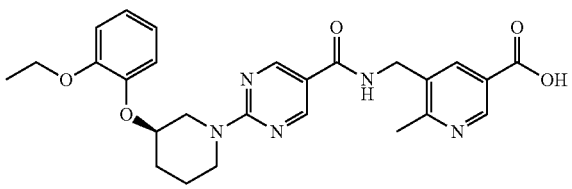 [SMILES: CCOc1ccccc1O[C@@H]1CCCN(c2ncc(C(=O)NCc3cc(C(=O)O)cnc3C)cn2)C1]

(R)-5-((2-(3-(2-ethoxyphenoxy)piperidin-1-yl)pyrimidine-5-carboxamido)methyl)-6-methylnicotinic acid was prepared from (R)-2-(3-(2-ethoxyphenoxy)piperidin-1-yl)pyrimidine-5-carboxylic acid and ethyl 5-(aminomethyl)-6-methylnicotinate using Amidation Method 2 (EDCI) and Ester Hydrolysis Method 1 (LiOH). $^1$H NMR (400 MHz, DMSO-$d_6$) δ 9.17 (m, 1H), 8.95 (s, 1H), 8.80 (s, 2H), 8.45 (m, 1H), 7.03 (d, 1H), 6.90 (m, 3H), 4.58 (d, 2H), 4.35 (m, 1H), 4.12 (m, 1H), 3.90 (m, 5H), 2.79 (s, 3H), 2.03 (m, 1H), 1.87 (m, 2H), 1.52 (m, 1H), 1.21 (t, 3H). MS (ES+) 492.2 (M+H).

Example 13. (R)-4-((2-(3-(2-ethoxyphenoxy)piperidin-1-yl)pyrimidine-5-carboxamido)methyl)-3-methylbenzoic acid

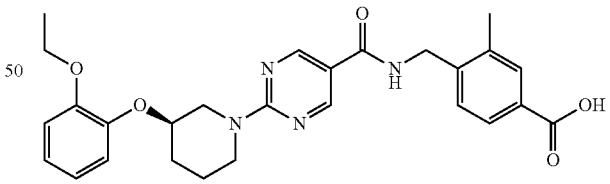

(R)-4-((2-(3-(2-ethoxyphenoxy)piperidin-1-yl)pyrimidine-5-carboxamido)methyl)-3-methylbenzoic acid was prepared from (R)-2-(3-(2-ethoxyphenoxy)piperidin-1-yl)pyrimidine-5-carboxylic acid and methyl 4-(aminomethyl)-3-methylbenzoate using Amidation Method 2 (EDCI) and Ester Hydrolysis Method 1 (LiOH). $^1$H NMR (400 MHz, DMSO-$d_6$) δ 12.8 (s, 1H), 8.81 (m, 1H), 8.78 (s, 2H), 7.75 (m, 2H), 7.31 (d, 1H), 7.05 (d, 1H), 6.91 (m, 3H), 4.48 (d, 2H), 4.33 (m, 1H), 4.18 (app dd, 1H), 3.90 (m, 4H), 3.80 (m, 1H), 2.36 (s, 3H), 2.05 (m, 1H), 1.85 (m, 2H), 1.52 (m, 1H), 1.21 (t, 3H). MS (ES+) 491 (M+H).

Example 14. (R)-3-((2-(3-(2-ethoxyphenoxy)piperidin-1-yl)pyrimidine-5-carboxamido)methyl)-2-methoxybenzoic acid

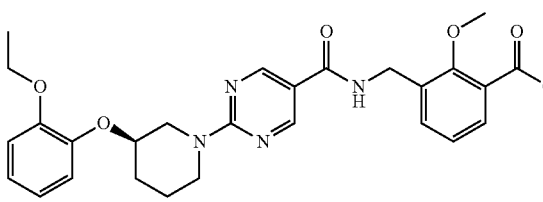

(R)-3-((2-(3-(2-ethoxyphenoxy)piperidin-1-yl)pyrimidine-5-carboxamido)methyl)-2-methoxybenzoic acid was prepared from (R)-2-(3-(2-ethoxyphenoxy)piperidin-1-yl)pyrimidine-5-carboxylic acid and ethyl 3-(aminomethyl)-2-methoxybenzoate hydrochloride using Amidation Method 1 (HATU) and Ester Hydrolysis Method 1 (LiOH). $^1$H NMR (300 MHz, DMSO-$d_6$) δ 12.6 (s, 1H), 8.78 (s, 3H), 7.88 (d, 1H), 7.78 (s, 1H), 7.10 (d, 1H), 7.05 (d, 1H), 6.90 (m, 3H), 4.45 (d, 2H), 4.36 (m, 1H), 4.18 (d, 1H), 3.90 (m, 8H), 2.05 (m, 1H), 1.87 (m, 2H), 1.52 (m, 1H), 1.21 (t, 3H). MS (ES+) 507.0 (M+H).

Example 15. 2-(4-((2-((R)-3-(2-ethoxyphenoxy)piperidin-1-yl)pyrimidine-5-carboxamido)methyl)phenyl)propanoic acid

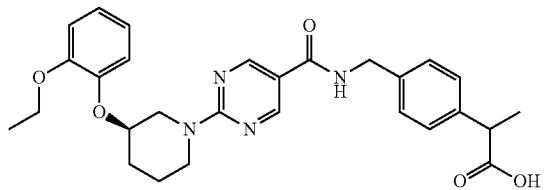 [SMILES: CCOc1ccccc1O[C@@H]1CCCN(c2ncc(C(=O)NCc3ccc(C(C)C(=O)O)cc3)cn2)C1]

2-(4-((2-((R)-3-(2-ethoxyphenoxy)piperidin-1-yl)pyrimidine-5-carboxamido)methyl)phenyl)propanoic acid was prepared from (R)-2-(3-(2-ethoxyphenoxy)piperidin-1-yl)pyrimidine-5-carboxylic acid and ethyl 2-(3-(aminomethyl)phenyl)propanoate hydrochloride using Amidation Method 2 (EDCI) and Ester Hydrolysis Method 1 (LiOH). 2-(4-((2-((R)-3-(2-Ethoxyphenoxy)piperidin-1-yl)pyrimidine-5-carboxamido)methyl)phenyl)propanoic acid was isolated by chiral SFC purification: Chiralcel-OJ-H, 5p, 1.0×25 cm, MeOH/CO$_2$ (20/80), T=35° C.; retention time, Example 15 diasteromer 7.056 min, other diastereomer 7.773 min. $^1$H NMR (500 MHz, DMSO-$d_6$) δ 12.25 (br s, 1H), 8.84 (app t, 1H), 8.76 (s, 2H), 7.25 (m, 4H), 7.04 (m, 1H), 6.90 (m, 3H), 4.43 (d, 2H), 4.31 (m, 1H), 4.19 (dd, 1H), 3.91 (m, 4H), 3.78 (m, 1H), 3.65 (q, 1H), 2.02 (m, 1H), 1.84 (m, 2H), 1.52 (m, 1H), 1.35 (d, 3H), 1.22 (t, 3H). MS (ES+) 505.2 (M+H).

Example 16. (R)-3-((2-(3-(2-ethoxyphenoxy)piperidin-1-yl)pyrimidine-5-carboxamido)methyl)-5-methylbenzoic acid

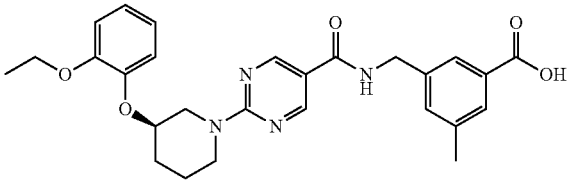 [SMILES: CCOc1ccccc1O[C@@H]1CCCN(c2ncc(C(=O)NCc3cc(C)cc(C(=O)O)c3)cn2)C1]

Step 1. Methyl (R)-3-((2-(3-(2-ethoxyphenoxy)piperidin-1-yl)pyrimidine-5-carboxamido)methyl)-5-methylbenzoate Methyl (R)-3-((2-(3-(2-ethoxyphenoxy)piperidin-1-yl)pyrimidine-5-carboxamido)methyl)-5-methylbenzoate was prepared from (R)-2-(3-(2-ethoxyphenoxy)piperidin-1-yl)pyrimidine-5-carboxylic acid and methyl 3-(aminomethyl)-5-methylbenzoate hydrochloride using Amidation Method 2 (EDCI).

Step 2. (R)-3-((2-(3-(2-ethoxyphenoxy)piperidin-1-yl)pyrimidine-5-carboxamido)methyl)-5-methylbenzoic acid Aqueous 1N sodium hydroxide solution (1.2 mL, 1.2 mmol) was added to a solution of methyl (R)-3-((2-(3-(2-ethoxyphenoxy)piperidin-1-yl)pyrimidine-5-carboxamido)methyl)-5-methylbenzoate (123 mg, 0.24 mmol) in THF (5 mL). The reaction mixture was heated to 60° C. for 48 hours, and then the volatiles were evaporated under reduced pressure. The remaining aqueous phase was washed with diethyl ether (10 mL). The aqueous phase was then adjusted to pH 3 with aqueous 1N HCl (1 mL), and then was extracted with EtOAc (2 times with 10 mL). The combined organic phases were washed with brine (2 times with 10 mL), dried over MgSO$_4$, filtered, and concentrated to provide (R)-3-((2-(3-(2-ethoxyphenoxy)piperidin-1-yl)pyrimidine-5-carboxamido)methyl)-5-methylbenzoic acid (84.4 mg, 60%). $^1$H NMR (500 MHz, CDCl$_3$) δ 8.77 (br s, 2H), 7.84 (s, 1H), 7.81 (s, 1H), 7.41 (s, 1H), 7.00 (d, 1H), 6.95 (m, 1H), 6.87 (m, 2H), 6.48 (br s, 1H), 4.65 (d, 2H), 4.42 (m, 1H), 4.27 (m, 1H), 4.13 (m, 1H), 4.00 (m, 2H), 3.85 (m, 1H), 3.71 (m, 1H), 2.40 (s, 3H), 2.11 (m, 1H), 1.97 (m, 2H), 1.60 (m, 1H), 1.38 (t, 3H). MS (ES+) 491.1 (M+H).

Example 17. (R)-2-(3-(4-cyano-2-ethoxyphenoxy)piperidin-1-yl)-N-ethylpyrimidine-5-carboxamide

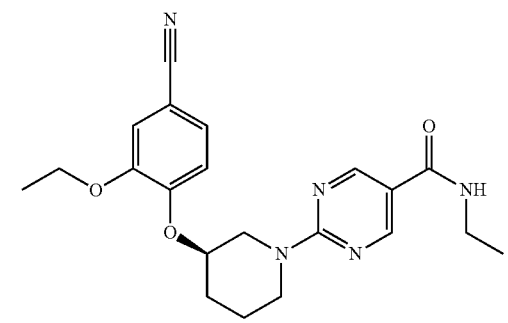 [SMILES: CCNC(=O)c1cnc(N2CCC[C@@H](Oc3ccc(C#N)cc3OCC)C2)nc1]

Step 1. 2-Chloro-N-ethylpyrimidine-5-carboxamide

A solution of ethylamine (4.26 g, 0.0946 mol) and triethylamine (28.7 g, 0.284 mol) in dichloromethane (75 mL), pre-cooled to −15 to −10° C., was added dropwise to a solution of 2-chloropyrimidine-5-carbonyl chloride (16.64 g, 0.0946 mmol) in dry dichloromethane (250 mL) at −15° C., then the reaction mixture was stirred at −15° C. for 1 hour. The reaction was quenched by the addition of a solution of concentrated hydrochloric acid (32.3 mL) in water (300 mL). The resulting mixture was stirred at room temperature for 1 hour. The layers were separated, and the aqueous phase was further extracted with dichloromethane (3×200 mL). The combined organic extracts were dried over Na$_2$SO$_4$, filtered, and concentrated. The crude residue was purified via column chromatography to provide 2-chloro-N-ethylpyrimidine-5-carboxamide (12.75 g, 72%).

Step 2. (S)—N-ethyl-2-(3-hydroxypiperidin-1-yl)pyrimidine-5-carboxamide

Triethylamine (1.5 mL, 11 mmol) and 2-chloro-N-ethylpyrimidine-5-carboxamide (830 mg, 4.47 mmol) were added sequentially to a solution of (S)-piperidin-3-ol hydrochloride (677 mg, 4.92 mmol) in acetonitrile (25 mL) at 20-25° C. The reaction mixture was heated to 80° C. for 16 hours. The mixture was then cooled to 20-25° C. and was concentrated under reduced pressure. The resulting residue was dissolved in EtOAc (25 mL) and washed with saturated NH$_4$Cl (10 mL) and brine (10 mL). The organic phase was dried over Na$_2$SO$_4$, filtered, and concentrated to provide (S)—N-ethyl-2-(3-hydroxypiperidin-1-yl)pyrimidine-5-carboxamide (827 mg, 73%).

Step 3. (R)-2-(3-(4-cyano-2-ethoxyphenoxy)piperidin-1-yl)-N-ethylpyrimidine-5-carboxamide A solution of triphenylphosphine (65 mg, 0.25 mmol) in THF (1 mL) and a solution of bis(2-methoxyethyl) (E)-diazene-1,2-dicarboxylate (56 mg, 0.24 mmol) in THF (1 mL) were added sequentially to a solution of 3-ethoxy-4-hydroxybenzonitrile (26 mg, 0.16 mmol) and (S)—N-ethyl-2-(3-hydroxypiperidin-1-yl)pyrimidine-5-carboxamide (40 mg, 0.16 mmol) in THF (2 mL) at 20-25° C. The reaction mixture was stirred at 20-25° C. for 16 hours. The mixture was diluted with ether (30 mL), and was washed sequentially with aqueous 1N NaOH solution (1 mL) and brine (1 mL). The organic phase was dried over MgSO$_4$, filtered, and concentrated to provide a crude residue, which was purified via preparative HPLC to afford (R)-2-(3-(4-cyano-2-ethoxyphenoxy)piperidin-1-yl)-N-ethylpyrimidine-5-carboxamide. HPLC: Waters XBridge dC18 4.6×50 mm, 5 μm, 95% water/5% acetonitrile linear to 5% water/95% acetonitrile over 4.0 min, 0.03% NH$_4$OH modifier, 2 mL/min; retention time 2.60 min. MS (ES+) 396.1 (M+H).

Examples 18. The Examples in the Following Table were Prepared and Analyzed by the Methods Described Below

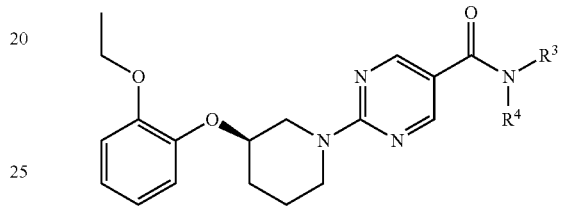

A solution of (R)-2-(3-(2-ethoxyphenoxy)piperidin-1-yl)pyrimidine-5-carboxylic acid in DMF (0.3M, 0.50 mL, 0.15 mmol), triethylamine (0.062 mL, 0.45 mmol) and a solution of HATU in DMF (0.3M, 0.50 mL, 0.15 mmol) were added sequentially to a vial containing the appropriate aminomethyl ester starting material (0.15 mmol). The vial was shaken and heated at 60° C. for 16 hours. The solvent was then evaporated under reduced pressure. To the resulting residue were added methanol (1.0 mL) and aqueous 4.5M sodium hydroxide solution (0.20 mL, 0.90 mmol). The vial was shaken and heated at 50° C. for 16 hours. Aqueous 1M hydrochloric acid solution was added to adjust the pH of the solution to approximately 7-8. The solvent was evaporated under reduced pressure. DMSO was added to the resulting residue and the solids were removed by filtration. The filtrate was purified by preparative HPLC to afford the specified products.

Analytical method: Xbridge C18, 2.1×50 mm, 5 μm, 50° C., Mobile Phase A 0.0375% TFA in water, Mobile Phase B 0.01875% TFA in acetonitrile, Gradient: 0.00 min 10% B, 0.50 min 10% B, 4.00 min 100% B, 0.8 mL/min, API-ES+

| Example | Compound Name | —NR$^3$R$^4$ | MS (ES+) (M + H) | Retention Time (min) |
|---|---|---|---|---|
| 18.1 | (R)-4-((2-(3-(2-ethoxyphenoxy)piperidin-1-yl)pyrimidine-5-carboxamido)methyl)benzoic acid | | 477 | 2.951 |

| Example | Compound Name | —NR³R⁴ | MS (ES+) (M + H) | Retention Time (min) |
|---|---|---|---|---|
| 18.2 | (R)-2-(3-((2-(3-(2-ethoxyphenoxy)piperidin-1-yl)pyrimidine-5-carboxamido)methyl)phenyl)acetic acid | | 491 | 2.974 |
| 18.3 | (R)-2-(2-((2-(3-(2-ethoxyphenoxy)piperidin-1-yl)pyrimidine-5-carboxamido)methyl)phenyl)acetic acid | | 491 | 3.041 |

Examples 19. The Examples in the Following Table were Prepared and Analyzed by the Methods Described Below

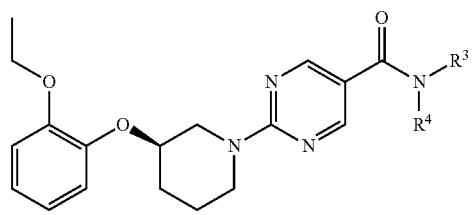

Amidation Procedure: HATU Method

A solution of (R)-2-(3-(2-ethoxyphenoxy)piperidin-1-yl)pyrimidine-5-carboxylic acid in DMF (0.2M, 0.50 mL, 0.10 mmol), triethylamine (0.060 mL, 0.40 mmol) and a solution of HATU in DMF (0.2M, 0.50 mL, 0.10 mmol) were added sequentially to a vial containing the appropriate amine (0.10 mmol). The vial was shaken and heated at 50° C. for 16 hours. The solvent was then evaporated under reduced pressure, and the resulting residue was purified by preparative HPLC to afford the specified product.

Amidation Procedure: DMC Method

A solution of (R)-2-(3-(2-ethoxyphenoxy)piperidin-1-yl)pyrimidine-5-carboxylic acid in DMF (0.2M, 0.50 mL, 0.10 mmol), triethylamine (0.060 mL, 0.40 mmol) and a solution of 2-chloro-1,3-dimethylimidazolinium chloride (DMC) in dichloromethane (0.3M, 0.50 mL, 0.15 mmol) were added sequentially to a vial containing the appropriate amine starting material (0.10 mmol). The vial was shaken and heated at 30° C. for 16 hours. The solvent was then evaporated under reduced pressure, and the resulting residue was purified by preparative HPLC to afford the specified product.

Analytical Methods:

Method A: Xbridge C18, 2.1×50 mm, 5 µm, 50° C., Mobile Phase A 0.0375% TFA in water, Mobile Phase B 0.01875% TFA in acetonitrile, Gradient: 0.00 min 1% B, 0.60 min 5% B, 4.00 min 100% B, 0.8 mL/min, API-ES+.

Method B: Xbridge C18, 2.1×50 mm, 5 µm, 50° C., Mobile Phase A 0.0375% TFA in water, Mobile Phase B 0.01875% TFA in acetonitrile, Gradient: 0.00 min 10% B, 0.50 min 10% B, 4.00 min 100% B, 0.8 mL/min, API-ES+.

| Example | Compound Name | —NR³R⁴ | Amidation Procedure | MS (ES+) (M + H) | Retention Time (min) and Analytical Method |
|---|---|---|---|---|---|
| 19.1 | (R)-(2-(3-(2-ethoxyphenoxy)piperidin-1-yl)pyrimidin-5-yl)(morpholino)methanone | | HATU | 413 | 3.112 (Method A) |
| 19.2 | (R)-2-(3-(2-ethoxyphenoxy)piperidin-1-yl)-N-((3-hydroxyisoxazol-5-yl)methyl)pyrimidine-5-carboxamide | | HATU | 440 | 2.998 (Method A) |

-continued

| Example | Compound Name | —NR³R⁴ | Amidation Procedure | MS (ES+) (M + H) | Retention Time (min) and Analytical Method |
|---|---|---|---|---|---|
| 19.3 | (R)-2-(3-(2-ethoxyphenoxy)piperidin-1-yl)-N-(isoxazol-3-ylmethyl)pyrimidine-5-carboxamide | | HATU | 424 | 3.136 (Method A) |
| 19.4 | (R)-N-(cyclopropylmethyl)-2-(3-(2-ethoxyphenoxy)piperidin-1-yl)pyrimidine-5-carboxamide | | HATU | 397 | 3.147 (Method B) |
| 19.5 | (R)-N-(2-amino-2-iminoethyl)-2-(3-(2-ethoxyphenoxy)piperidin-1-yl)pyrimidine-5-carboxamide | | HATU | 399 | 2.656 (Method A) |
| 19.6 | (R)-(2-(3-(2-ethoxyphenoxy)piperidin-1-yl)pyrimidin-5-yl)(1-methyl-4,6-dihydropyrrolo[3,4-c]pyrazol-5(1H)-yl)methanone | | HATU | 449 | 3.094 (Method A) |
| 19.7 | (R)-N-benzyl-2-(3-(2-ethoxyphenoxy)piperidin-1-yl)pyrimidine-5-carboxamide | | HATU | 433 | 3.32 (Method B) |
| 19.8 | (R)-2-(3-(2-ethoxyphenoxy)piperidin-1-yl)-N-(2-(methylsulfonyl)ethyl)pyrimidine-5-carboxamide | | HATU | 449 | 2.961 (Method A) |
| 19.9 | (R)-(2-(3-(2-ethoxyphenoxy)piperidin-1-yl)pyrimidin-5-yl)(3-methoxyazetidin-1-yl)methanone | | HATU | 413 | 3.163 (Method A) |
| 19.10 | (R)-N-(2-(1H-1,2,4-triazol-1-yl)ethyl)-2-(3-(2-ethoxyphenoxy)piperidin-1-yl)pyrimidine-5-carboxamide | | HATU | 438 | 2.847 (Method A) |
| 19.11 | (R)-azetidin-1-yl(2-(3-(2-ethoxyphenoxy)piperidin-1-yl)pyrimidin-5-yl)methanone | | HATU | 383 | 3.158 (Method A) |
| 19.12 | (R)-(2-(3-(2-ethoxyphenoxy)piperidin-1-yl)pyrimidin-5-yl)(isoindolin-2-yl)methanone | | HATU | 445 | 3.435 (Method B) |

-continued

| Example | Compound Name | —NR³R⁴ | Amidation Procedure | MS (ES+) (M + H) | Retention Time (min) and Analytical Method |
|---|---|---|---|---|---|
| 19.13 | 2-((R)-3-(2-ethoxy-phenoxy)piperidin-1-yl)-N-((R)-5-oxopyrrolidin-3-yl)pyrimidine-5-carboxamide | | HATU | 426 | 2.818 (Method A) |
| 19.14 | ((1R,4R)-2-oxa-5-azabicyclo[2.2.1]heptan-5-yl)(2-((R)-3-(2-ethoxyphenoxy)piperidin-1-yl)pyrimidin-5-yl)methanone | | HATU | 425 | 3.043 (Method A) |
| 19.15 | (R)-2-(3-(2-ethoxyphenoxy)piperidin-1-yl)-N-(oxazol-4-ylmethyl)pyrimidine-5-carboxamide | | HATU | 424 | 3.03 (Method A) |
| 19.16 | 2-((R)-3-(2-ethoxy-phenoxy)piperidin-1-yl)-N-((S)-5-oxopyrrolidin-3-yl)pyrimidine-5-carboxamide | | HATU | 426 | 2.817 (Method A) |
| 19.17 | (R)-N-(4-amino-2-methyl-4-oxobutan-2-yl)-2-(3-(2-ethoxyphenoxy)piperidin-1-yl)pyrimidine-5-carboxamide | | HATU | 442 | 2.997 (Method A) |
| 19.18 | (R)-2-(3-(2-ethoxyphenoxy)piperidin-1-yl)-N-(pyrazin-2-ylmethyl)pyrimidine-5-carboxamide | | HATU | 435 | 2.979 (Method A) |
| 19.19 | (R)-2-(3-(2-ethoxyphenoxy)piperidin-1-yl)-N-(isoxazol-3-yl)pyrimidine-5-carboxamide | | DMC | 410 | 3.303 (Method A) |
| 19.20 | (R)-2-(3-(2-ethoxyphenoxy)piperidin-1-yl)-N-(pyrimidin-5-yl)pyrimidine-5-carboxamide | | DMC | 421 | 3.088 (Method A) |
| 19.21 | (R)-2-(3-(2-ethoxy-phenoxy)piperidin-1-yl)-N-(1-hydroxy-2-methyl-propan-2-yl)pyrimidine-5-carboxamide | | HATU | 415 | 3.11 (Method A) |
| 19.22 | (R)-N-cyclobutyl-2-(3-(2-ethoxyphenoxy)piperidin-1-yl)pyrimidine-5-carboxamide | | HATU | 397 | 3.174 (Method B) |

Examples 20. The Examples in the Following Table were Prepared and Analyzed by the Methods Described Below

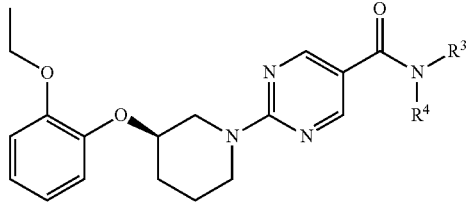

A solution of HBTU in DMF (0.5M, 0.125 mmol), N,N-diisopropylethylamine (0.375 mmol), and the appropriate amine starting material (0.125 mmol) were added sequentially to a vial containing a solution of (R)-2-(3-(2-ethoxypyridin-3-yloxy)piperidin-1-yl)pyrimidine-5-carboxylic acid (0.125 mmol) in DMF (0.5 mL), and the resulting reaction mixture was shaken for 16 hours at room temperature. The solvent was evaporated under reduced pressure and the resulting residue was partitioned between ethyl acetate (1 mL) and water (1 mL). The organic layer was concentrated under reduced pressure and the resulting residue was purified by preparative HPLC to afford the title compound. Analytical method: Acquity UPLC BEH C18, 2.1×50 mm, 1.7 μm, 50° C., Mobile Phase A 10 mM NH$_4$OAc in 95% water and 5% acetonitrile, Mobile Phase B 10 mM NH$_4$OAc in 5% water and 95% acetonitrile, Gradient: 0.00 min 100% A, 1.20 min 100% B, 1.47 min 100% B, 1.0 mL/min, API-ES+.

| Example | Compound Name | —NR$^3$R$^4$ | MS (ES+) (M + H) | Retention Time (min) |
|---|---|---|---|---|
| 20.1 | (R)-N-(3-amino-3-oxopropyl)-2-(3-(2-ethoxyphenoxy)piperidin-1-yl)pyrimidine-5-carboxamide | | 414.2 | 0.771 |
| 20.2 | (R)-N-(3-(2H-tetrazol-5-yl)propyl)-2-(3-(2-ethoxyphenoxy)piperidin-1-yl)pyrimidine-5-carboxamide | | 453.2 | 0.679 |
| 20.3 | (R)-2-(3-(2-ethoxyphenoxy)piperidin-1-yl)-N,N-dimethylpyrimidine-5-carboxamide | | 371.2 | 0.923 |
| 20.4 | (R)-2-(3-(2-ethoxyphenoxy)piperidin-1-yl)-N-(3-(methylamino)-3-oxopropyl)pyrimidine-5-carboxamide | | 428.2 | 0.795 |
| 20.5 | (R)-2-(3-(2-ethoxyphenoxy)piperidin-1-yl)-N-((5-oxo-2,5-dihydro-1H-1,2,4-triazol-3-yl)methyl)pyrimidine-5-carboxamide | | 440.2 | 0.749 |
| 20.6 | (R)-2-(3-(2-ethoxyphenoxy)piperidin-1-yl)-N-(2-(methylamino)-2-oxoethyl)pyrimidine-5-carboxamide | | 414.2 | 0.792 |
| 20.7 | (R)-(3,3-difluoroazetidin-1-yl)(2-(3-(2-ethoxyphenoxy)piperidin-1-yl)pyrimidin-5-yl)methanone | | 419.1 | 1.013 |
| 20.8 | (R)-2-(3-(2-ethoxyphenoxy)piperidin-1-yl)-N-(2-(5-hydroxy-1H-pyrazol-4-yl)ethyl)pyrimidine-5-carboxamide | | 453.2 | 0.779 |

-continued

| Example | Compound Name | —NR³R⁴ | MS (ES+) (M + H) | Retention Time (min) |
|---|---|---|---|---|
| 20.9 | (R)-(2-(3-(2-ethoxyphenoxy)piperidin-1-yl)pyrimidin-5-yl)(pyrrolidin-1-yl)methanone | | 397.2 | 0.976 |
| 20.10 | (S)-1-(2-((R)-3-(2-ethoxyphenoxy)piperidin-1-yl)pyrimidine-5-carbonyl)azetidine-2-carboxamide | | 426.2 | 0.808 |
| 20.11 | (R)-(2-(3-(2-ethoxyphenoxy)piperidin-1-yl)pyrimidin-5-yl)(piperidin-1-yl)methanone | | 411.2 | 1.067 |

Examples 21. The Examples in the Following Table were Prepared and Analyzed by the Methods Described Below

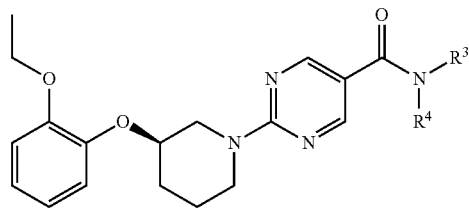

A solution of (R)-2-(3-(2-ethoxyphenoxy)piperidin-1-yl)pyrimidine-5-carboxylic acid in DMF (0.2M, 0.10 mmol), a solution of HATU in DMF (0.2M, 0.15 mmol), and triethylamine (0.30 mmol) were added sequentially to a vial containing a solution of the appropriate amine (0.10 mmol), and the resulting reaction mixture was shaken for 16 hours at room temperature. The solvent was evaporated under reduced pressure and the resulting residue was partitioned between dichloromethane and water. The organic layer was concentrated under reduced pressure and the resulting residue was purified by preparative HPLC to afford the title compound.

Analytical method: Acquity UPLC BEH C18, 2.1×50 mm, 1.7 μm, 50° C., Mobile Phase A 10 mM NH₄OAc in 95% water and 5% acetonitrile, Mobile Phase B 10 mM NH₄OAc in 5% water and 95% acetonitrile, Gradient: 0.00 min 100% A, 1.20 min 100% B, 1.47 min 100% B, 1.0 mL/min, API-ES+.

| Example | Compound Name | —NR³R⁴ | MS (ES+) (M + H) | Retention Time (min) |
|---|---|---|---|---|
| 21.1 | N-((S)-2,3-dihydro-1H-inden-1-yl)-2-((R)-3-(2-ethoxyphenoxy)piperidin-1-yl)pyrimidine-5-carboxamide | | 459.3 | 1.111 |
| 21.2 | (R)-(2-(3-(2-ethoxyphenoxy)piperidin-1-yl)pyrimidin-5-yl)(3-phenoxyazetidin-1-yl)methanone | | 475.3 | 1.112 |

Pharmacological Data

The following protocols may of course be varied by those skilled in the art.

Generation of Human DGAT2 (hDGAT2) Construct

A construct for hDGAT2 was generated with an N-terminal FLAG tag (an octapeptide with the amino acid sequence of AspTyrLysAspAspAspAspLys). For the FLAG-tagged hDGAT2 construct, the cDNA for hDGAT2 was custom-synthesized at Genscript and cloned into the pFastBac1 vector (Invitrogen) by using BamHI/XhoI restriction enzymes to generate an N-terminally FLAG-tagged pFast-Bac1-FLAG-hDGAT2 construct (amino acids 1-388). The construct was confirmed by sequencing in both directions.

DGAT2 Expression and Preparation of the DGAT2 Membrane Fraction

Recombinant baculovirus for the FLAG-tagged hDGAT2 was generated in SF9 insect cells using Bac-to-Bac baculovirus expression system (Invitrogen) according to the manufacturer's protocol. For the expression of hDGAT2, SF9 cells (20 L) grown in Sf900II media were infected with hDGAT2 baculovirus at a multiplicity of infection of 1 in a Wave Bioreactor System 20/50P wave bag (GE Healthcare). After 40 hours of infection, the cells were then harvested by centrifugation at 5,000×g. The cell pellets were washed by resuspending in phosphate buffered saline (PBS) and collected by centrifugation at 5,000×g. The cell paste was flash frozen in liquid $N_2$ and stored at −80° C. until needed. All operations below were at 4° C. unless otherwise noted. The cells were resuspended in lysis buffer (50 mM Tris-HCl, pH 8.0, 250 mM sucrose) including 1 mM ethylenediaminetetraacetic acid (EDTA) and the complete protease inhibitor cocktail (Roche Diagnostics) at a ratio of 3 ml buffer per 1 g cell paste. The cells were lysed by dounce homogenizer. The cell debris was removed by centrifugation at 1,000×g for 20 min, and the supernatant was centrifuged at 100,000×g for 1 hour. The resulting pellet was rinsed three times by filling ultracentrifuge tubes to the top with ice cold PBS before decanting. The washed pellet was resuspended with gentle stirring for 1 hour in lysis buffer containing 8 mM 3-[(3-cholamidopropyl)dimethylammonio]-1-propanesulfonate (CHAPS) at a ratio of 1 ml buffer per 1 g of original cell paste and centrifuged again at 100,000×g for 1 hour. The resulting supernatant was aliquoted, flash frozen in liquid $N_2$, and stored at −80° C. until use.

In Vitro DGAT2 Assay and Determination of $IC_{50}$ Values for DGAT2 Inhibitors For determination of $IC_{50}$ values, the reactions were carried out in 384-well white Polyplates (Perkin Elmer) in a total volume of 20 µL. To 14 of compounds dissolved in 100% DMSO and spotted at the bottom of each well, 5 µL of 0.04% bovine serum albumin (BSA) (fatty acid free, Sigma Aldrich) was added and the mixture was incubated at room temperature for 20 minutes. To this mixture, 10 µL of hDGAT2 membrane fraction (0.01 mg/mL) diluted in 100 mM Hepes-NaOH, pH 7.4, 20 mM $MgCl_2$ containing 200 nM methyl arachidonyl fluorophosphonate (Cayman Chemical; dried from ethyl acetate stock solution under argon gas and dissolved in DMSO as 5 mM stock) was added. After this mixture was preincubated at room temperature for 2 hours, DGAT2 reactions were initiated by the addition of 4 µL of substrates containing 30 µM [1-$^{14}$C]decanoyl-CoA (custom-synthesized by Perkin Elmer, 50 mCi/mmol) and 125 µM 1,2-didecanoyl-sn-glycerol (Avanti Polar Lipids) dissolved in 12.5% acetone. The reaction mixtures were incubated at room temperature for 40 min and the reactions were stopped by addition of 5 µL of 1% $H_3PO_4$. After the addition of 45 µL MicroScint-E (Perkin-Elmer), plates were sealed with Top Seal-A covers (Perkin-Elmer) and phase partitioning of substrates and products was achieved using a HT-91100 microplate orbital shaker (Big Bear Automation, Santa Clara, Calif.). Plates were centrifuged at 2,000×g for 1 min in an Allegra 6R Centrifuge (Beckman Coulter) and then were sealed again with fresh covers before reading in a 1450 Microbeta Wallac Trilux Scintillation Counter (Perkin Elmer). DGAT2 activity was measured by quantifying the generated product [$^{14}$C]tridecanoylglycerol in the upper organic phase.

Background activity obtained using 50 µM of (1R, 2R)-2-({3'-Fluoro-4'-[(6-fluoro-1, 3-benzothiazol-2-yl)amino]-1,1'-biphenyl-4-yl}carbonyl)cyclopentanecarboxylic acid (US 20040224997, Example 26) or (R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone (WO 2013150416, Example 196-A) for complete inhibition of DGAT2 was subtracted from all reactions. Inhibitors were tested at eleven different concentrations to generate $IC_{50}$ values for each compound. The eleven inhibitor concentrations employed typically included 50, 15.8, 5, 1.58, 0.50, 0.16, 0.05, 0.016, 0.005, 0.0016, and 0.0005 µM. The data were plotted as percentage of inhibition versus inhibitor concentration and fit to the equation, $y=100/[1+(x/IC_{50})^z]$, where $IC_{50}$ is the inhibitor concentration at 50% inhibition and z is the Hill slope (the slope of the curve at its inflection point).

Table 3 below provides the $IC_{50}$ values of the Examples for inhibition of DGAT2 in accordance with the above-described assay. Results are reported as geometric mean $IC_{50}$ values.

TABLE 3

$IC_{50}$ values of Examples for inhibition of DGAT2

| Example number | $IC_{50}$ (nM) |
|---|---|
| 1 | 91.6 |
| 2 | 123 |
| 3 | 88.4 |
| 4 | 35 |
| 5 | 66.6 |
| 6 | 222 |
| 7 | 149 |
| 8 | 9.7 |
| 9 | 38.1 |
| 10 | 87.3 |
| 11 | 122 |
| 12 | 62.3 |
| 13 | 45.2 |
| 14 | 76.6 |
| 15 | 2.4 |
| 16 | 47.7 |
| 17 | 182 |
| 18.1 | 165 |
| 18.2 | 156 |
| 18.3 | 182 |
| 19.1 | 22.6 |
| 19.2 | 262 |
| 19.3 | 10.8 |
| 19.4 | 18.6 |
| 19.5 | 124 |
| 19.6 | 34.9 |
| 19.7 | 4.3 |
| 19.8 | 102 |

TABLE 3-continued

IC$_{50}$ values of Examples for inhibition of DGAT2

| Example number | IC$_{50}$ (nM) |
|---|---|
| 19.9 | 14.3 |
| 19.10 | 32.4 |
| 19.11 | 26.7 |
| 19.12 | 1.4 |
| 19.13 | 46.7 |
| 19.14 | 21.5 |
| 19.15 | 11.2 |
| 19.16 | 122 |
| 19.17 | 12.2 |
| 19.18 | 22.5 |
| 19.19 | 11.1 |
| 19.20 | 33.3 |
| 19.21 | 7.9 |
| 19.22 | 10.7 |
| 20.1 | 149 |
| 20.2 | 431 |
| 20.3 | 104 |
| 20.4 | 53.3 |
| 20.5 | 68 |
| 20.6 | 144 |
| 20.7 | 7.9 |
| 20.8 | 29.3 |
| 20.9 | 24.5 |
| 20.10 | 170 |
| 20.11 | 15.7 |
| 21.1 | 1.5 |
| 21.2 | 0.6 |

TABLE 4

IC$_{50}$ values of selected DGAT2 inhibitors in primary human hepatocytes.

| Example number | IC$_{50}$ (nM) |
|---|---|
| 1 | 11.2 |
| 2 | 11.5 |
| 3 | 29.2 |
| 4 | 6.6 |
| 5 | 8.4 |
| 6 | 57.8 |
| 7 | 19.2 |
| 8 | 51.7 |
| 9 | 57 |
| 10 | 10.4 |
| 11 | 6.8 |
| 12 | 67.5 |
| 13 | 20.7 |
| 15 | 78.8 |
| 16 | 45 |
| 17 | 19.8 |
| 18.1 | 116 |
| 18.2 | 45.7 |
| 18.3 | 499 |
| 19.2 | 341 |
| 20.5 | 81.6 |
| 20.8 | 37.8 |
| 20.10 | 59.8 |

Determination of IC$_{50}$ Values for DGAT2 Inhibitors in Human Hepatocytes

For evaluation of the effects of DGAT2 inhibitors in a cell-based setting, cryopreserved human hepatocytes (Lot QOC and NON, Celsis, Chicago, Ill.) were thawed and plated onto type I collagen-coated plates according to the manufacturer's instructions. After 24 hours overnight recovery period, the cells were overlayed with media containing 250 µg/ml Matrigel (BD Biosciences, San Jose, Calif.). The following day, media was aspirated and replaced with serum-free Williams Media E (Life Technologies, Grand Island, N.Y.) containing 400 µM sodium dodecanoate (Sigma-Aldrich, St. Louis, Mo.). Forty minutes later, DGAT2 inhibitors (prepared as 100× stocks in 25% DMSO, 75% Williams' Media E) were added to the desired final concentration. All wells contained a selective DGAT1 inhibitor (Example 3, WO2009016462) at a concentration (3 µM) that completely suppressed endogenous DGAT1 activity. After a 20 minute preincubation, 0.2 µCi [1,3-$^{14}$C]-glycerol (American Radio Chemicals, St. Louis, Mo.) was added to each well and mixed by gentle pipetting prior to a 3 hour incubation. At this point, media was aspirated and the cells were lysed in isopropyl alcohol: tetrahydrofuran (9:1) prior to centrifugation at 3000 rpm for 5 minutes. Radiolabeled lipids were resolved using a 2-solvent system by thin layer chromatography using standard technique (solvent 1 contained ethyl acetate: isopropyl alcohol: chloroform: methanol: 0.25% potassium chloride in water (100:100:100: 40.2:36.1, v/v/v/v) and solvent 2 contained hexane: diethyl ether: acetic acid (70:27:3, v/v/v)). After separation, radiolabeled lipids were visualized using a Molecular Dynamics' PhosphorImager system. The half maximal inhibitory concentrations (IC$_{50}$ values) were determined using GraphPad Prism (GraphPad Software, Inc., La Jolla, Calif.).

Table 4 below provides IC$_{50}$ values for the Examples in accordance with the above-described assay. Results were reported as average IC$_{50}$ values, low and high IC$_{50}$ range (95% confidence interval).

Acute Effects of DGAT2 Inhibitors on Plasma TAG Levels

Blockade of hepatic DGAT2 activity has been shown to inhibit the secretion of VLDL TAG. To evaluate the acute effects of DGAT2 inhibitors on hepatic TAG production, male Sprague Dawley rats (~200 g, Harlan Laboratories Inc.) were fed a low fat, high-sucrose diet (TD03045, Harlan Laboratories Inc.) for 2 days prior to dosing with DGAT2 inhibitors. At this time, animals were fasted for 4 hours and compounds administered as a solution in 1% HPMC/40 mM Tris/1% HPMCAS. Two hours after treatment with DGAT2 inhibitors, blood was drawn from the lateral tail vein and plasma TAG levels determined using a Roche Hitachi Chemistry analyzer according to the manufacturer's instructions. Data were analyzed using GraphPad Prism (GraphPad Software, Inc., La Jolla, Calif.) and are shown as percent change from Vehicle-treated animals. Statistical analysis was performed using one-way ANOVA followed by Dunnett's multiple comparison test. *$p<0.05$, $p<0.001$, *$p<0.0001$.

FIG. 3 provides acute effects of DGAT2 inhibitors on plasma TAG levels in Sprague Dawley rats for the Examples 1, 3 and 15 in accordance with the above-described method.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating non-alcoholic fatty liver disease (NAFLD) in humans comprising the step of administering to a human in need of such treatment a therapeutically effective amount of a compound having the structure:

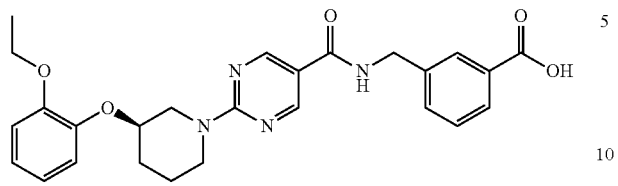

or a pharmaceutically acceptable salt thereof.

2. A method for treating non-alcoholic fatty liver disease (NAFLD), in humans comprising the step of administering to a human in need of such treatment a therapeutically effective amount of a compound comprising 3-((2-(3-(2-ethoxyphenoxy)piperidin-1-yl)pyrimidine-5-carboxamido)methyl)benzoic acid or (R)-3-((2-(3-(2-ethoxyphenoxy)piperidin-1-yl)pyrimidine-5-carboxamido)methyl)benzoic acid or a pharmaceutically acceptable salt thereof.

3. The method according to claim 1 wherein said compound or pharmaceutically acceptable salt thereof is in admixture with at least one pharmaceutically acceptable excipient.

4. The method according to claim 2 wherein said compound or pharmaceutically acceptable salt thereof is in admixture with at least one pharmaceutically acceptable excipient.

* * * * *